(12) United States Patent
Page et al.

(10) Patent No.: US 12,180,547 B2
(45) Date of Patent: Dec. 31, 2024

(54) DETECTION OF EXPRESSION OF MARKERS USEFUL FOR PREDICTING RISK OF CATASTROPHIC INJURIES IN ATHLETIC ANIMALS

(71) Applicant: University of Kentucky Research Foundation, Lexington, KY (US)

(72) Inventors: Allen E. Page, Wilmore, KY (US); David W. Horohov, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 173 days.

(21) Appl. No.: 17/198,897

(22) Filed: Mar. 11, 2021

(65) Prior Publication Data
US 2021/0285048 A1 Sep. 16, 2021

Related U.S. Application Data

(60) Provisional application No. 63/119,498, filed on Nov. 30, 2020, provisional application No. 62/988,280, filed on Mar. 11, 2020.

(51) Int. Cl.
*C12Q 1/68* (2018.01)
*C12P 19/34* (2006.01)
*C12Q 1/6883* (2018.01)

(52) U.S. Cl.
CPC ..... *C12Q 1/6883* (2013.01); *C12Q 2600/156* (2013.01); *C12Q 2600/158* (2013.01)

(58) Field of Classification Search
CPC ............ C12Q 1/6883; C12Q 2600/156; C12Q 2600/158; C12Q 2600/124
See application file for complete search history.

(56) References Cited

PUBLICATIONS

S. Capomaccio, et al. "Microarray analysis after strenuous exercise in peripheral blood mononuclear cells of endurance horses" Anim Genet. Dec. 2010;41 Suppl 2:166-75 (Year: 2010).*
A.E. Karagianni, et al. "Comparative transcriptome analysis of equine alveolar macrophages" First published: Apr. 20, 2016, Equine Veterinary Journal, vol. 49, Issue 3, May 2017. (Year: 2016).*
Vivian G. Cheung, et al. "Natural variation in human gene expression assessed in lymphoblastoid cells" Nature Genetics, Mar. 2003, vol. 33, pp. 422-425. (Year: 2003).*
J. Perren Cobb, et al. "Sepsis gene expression profiling: Murine splenic compared with hepatic responses determined by using complementary DNA microarrays" Crit Care Med 2002 vol. 30, No. 12 (Year: 2002).*
Guoan Chen, et al. "Discordant Protein and mRNA Expression in Lung Adenocarcinomas" Molecular & Cellular Proteomics 1.4, pp. 304-313, 2002 (Year: 2002).*
Yasushi Hoshikawa, et al. "Hypoxia induces different genes in the lungs of rats compared with mice" Physiol Genomics 12: 209-219, 2003 (Year: 2003).*
Hang-Ah Kim, et al. "Integrated analysis of microRNA and mRNA expressions in peripheral blood leukocytes of Warmblood horses before and after exercise" Journal of Veterinary Science 2018; 19(1): 99-106. Published online: Jan. 23, 2018 (Year: 2018).*
Katarzyna Ropka-Molik, et al. "Transcriptome profiling of Arabian horse blood during training regimens" BMC Genetics vol. 18, Article No. 31 (2017) (Year: 2017).*
GEO2r output for analysis of the GSE76310 dataset for ID:A_69_P004860 (IL1RN) for samples GSM1980071 and GSM1980072, printed from NCBI on Mar. 31, 2023, two pages. (Year: 2023).*
Núria Mach, et al. "Integrated mRNA and miRNA expression profiling in blood reveals candidate biomarkers associated with endurance exercise in the horse" Scientific Reports vol. 6, Article No. 22932 (2016) (Year: 2016).*
Nancy B.Y. Tsui, et al. "Stability of Endogenous and Added RNA in Blood Specimens, Serum, and Plasma", Clinical Chemistry, vol. 48, Issue 10, Oct. 1, 2002, pp. 1647-1653. (Year: 2002).*
Output of gene expression results from "Integrated mRNA and miRNA expression profiling in blood reveals candidate biomarkers associated with endurance exercise in horse (mRNA)" GSE72973 / GPL20908 / 13694, printed from https://www.ncbi.nlm.nih.gov/geo/geo2r/?acc=GSE72973, 2 pages printed on Jan. 30, 2024 (Year: 2024).*
Output of gene expression results from "Analysis of mRNA of leukocytes before and after exercise in 3 warmblood horses" GSE763103 / GPL15190 / A_69_P004860, printed from https://www.ncbi.nlm.nih.gov/geo/geo2r/?acc=GSE76310, 1 page printed on Jan. 30, 2024 (Year: 2024).*
Output of gene expression results from "Analysis of mRNA of leukocytes before and after exercise in 3 warmblood horses" GSE763103 / GPL15190 / A_69_P001236, printed from https://www.ncbi.nlm.nih.gov/geo/geo2r/?acc=GSE76310, 1 page printed on Jan. 30, 2024 (Year: 2024).*
Anderson, T.M., McIlwraith, C.W. and Douay, P. (2004) The role of conformation in musculoskeletal problems in the racing Thoroughbred. Equine Vet J 36, 571-575.
Anthenill, L.A., Gardner, I.A., Pool, R.R., Garcia, T.C. and Stover, S.M. (2010) Comparison of macrostructural and microstructural bone features in Thoroughbred racehorses with and without midbody fracture of the proximal sesamoid bone. Am J Vet Res 71, 755-765.
Anthenill, L.A., Stover, S.M., Gardner, I.A. and Hill, A.E. (2007) Risk factors for proximal sesamoid bone fractures associated with exercise history and horseshoe characteristics in Thoroughbred racehorses. Am J Vet Res 68, 760-771.
Anthenill, L.A., Stover, S.M., Gardner, I.A., Hill, A.E., Lee, C.M., Anderson, M.L., Barr, B.C., Read, D.H., Johnson, B.J., Woods, L.W., Daft, B.M., Kinde, H., Moore, J.D., Farman, C.A., Odani, J.S., Pesavento, P.A., Uzal, F.A., Case, J.T. and Ardans, A.A. (2006) Association between findings on palmarodorsal radiographic images and detection of a fracture in the proximal sesamoid bones of forelimbs obtained from cadavers of racing Thoroughbreds. American Journal of Veterinary Research 67, 858-868.

(Continued)

*Primary Examiner* — Stephen T Kapushoc
(74) *Attorney, Agent, or Firm* — Stites & Harbison PLLC; Gary N. Stewart; Mandy Wilson Decker

(57) ABSTRACT

The present disclosure relates to methods of detecting gene expression in a biological sample from an animal. More specifically, this disclosure relates to methods of detecting risk for a catastrophic injury in an animal, such as a non-human athletic animal, based on the expression of select genes within a biological sample from the animal, which can be determined using mRNA expression analysis.

10 Claims, 16 Drawing Sheets

Specification includes a Sequence Listing.

(56) References Cited

PUBLICATIONS

Barr, E.D., Pinchbeck, G.L., Clegg, P.D., Boyde, A. and Riggs, C.M. (2009) Post mortem evaluation of palmar osteochondral disease (traumatic osteochondrosis) of the metacarpo/metatarsophalangeal joint in Thoroughbred racehorses. 41, 366-371.

Billinghurst, R.C., Brama, P.A., van Weeren, P.R., Knowlton, M.S. and McIlwraith, C.W. (2003) Significant exercise-related changes in the serum levels of two biomarkers of collagen metabolism in young horses. Osteoarthritis Cartilage 11, 760-769.

Blott, S.C., Swinburne, J.E., Sibbons, C., Fox-Clipsham, L.Y., Helwegen, M., Hillyer, L., Parkin, T.D.H., Newton, J.R. and Vaudin, M. (2014) A genome-wide association study demonstrates significant genetic variation for fracture risk in Thoroughbred racehorses. BMC Genomics 15, 147.

Blumenfeld, I., Srouji, S., Peled, M. and Livne, E. (2002) Metalloproteinases (MMPs-2, -3) are involved in TGF-β and IGF-1-induced bone defect healing in 20-month-old female rats. Archives of Gerontology and Geriatrics 35, 59-69.

Brama, P.A., van den Boom, R., DeGroott, J., Kiers, G.H. and van Weeren, P.R. (2004) Collagenase-1 (MMP-1) activity in equine synovial fluid: influence of age, joint pathology, exercise and repeated arthrocentesis. Equine Vet J 36, 34-40.

Breathnach, C.C., Sturgill-Wright, T., Stiltner, J.L., Adams, A.A., Lunn, D.P. and Horohov, D.W. (2006) Foals are interferon gamma-deficient at birth. Vet Immunol Immunopathol 112, 199-209.

Carrier, T.K., Estberg, L., Stover, S.M., Gardner, I.A., Johnson, B.J., Read, D.H. and Ardans, A.A. (1998) Association between long periods without high-speed workouts and risk of complete humeral or pelvic fracture in thoroughbred racehorses: 54 cases (1991-1994). J Am Vet Med Assoc 212, 1582-1587.

Cohen, N.D., Berry, S.M., Peloso, J.G., Mundy, G.D. and Howard, I.C. (2000) Association of highspeed exercise with racing injury in thoroughbreds. J Am Vet Med Assoc 216, 1273-1278.

Cohen, N.D., Dresser, B.T., Peloso, J.G., Mundy, G.D. and Woods, A.M. (1999) Frequency of musculoskeletal injuries and risk factors associated with injuries incurred in Quarter Horses during races. J Am Vet Med Assoc 215, 662-669.

Cohen, N.D., Mundy, G.D., Peloso, J.G., Carey, V.J. and Amend, N.K. (1999) Results of physical inspection before races and race-related characteristics and their association with musculoskeletal injuries in Thoroughbreds during races. Journal of the American Veterinary Medical Association 215, 654-661.

Cohen, N.D., Peloso, J.G., Mundy, G.D., Fisher, M., Holland, R.E., Little, T.V., Misheff, M.M., Watkins, J.P., Honnas, C.M. and Moyer, W. (1997) Racing-related factors and results of prerace physical inspection and their association with musculoskeletal injuries incurred in thoroughbreds during races. J Am Vet Med Assoc 211, 454-463.

Costa, M.F., Davies, H.M., Anderson, G.A. and Slocombe, R.F. (2011) Effects of two training protocols on Angiotensin I-converting enzyme (ACE) activity in horses. Equine Vet J 43, 466-470.

Denoix, J.M. and Coudry, V. (2020) Clinical insights: Imaging of the equine fetlock in Thoroughbred racehorses: Identification of imaging changes to predict catastrophic injury. Equine Veterinary Journal 52, 342-343.

Donovan, D.C., Jackson, C.A., Colahan, P.T., Norton, N. and Hurley, D.J. (2007) Exercise-induced alterations in proinflammatory cytokines and prostaglandin F2alpha in horses. Vet Immunol Immunopathol 118, 263-269.

Estberg, L., Stover, S.M., Gardner, I.A., Drake, C.M., Johnson, B. and Ardans, A. (1996) Highspeed exercise history and catastrophic racing fracture in thoroughbreds. Am J Vet Res 57, 15491555.

Estberg, L., Stover, S.M., Gardner, I.A., Johnson, B.J., Jack, R.A., Case, J.T., Ardans, A., Read, D.H., Anderson, M.L., Barr, B.C., Daft, B.M., Kinde, H., Moore, J., Stoltz, J. and Woods, L. (1998) Relationship between race start characteristics and risk of catastrophic injury in thoroughbreds: 78 cases (1992).

Frisbie, D.D., Al-Sobayil, F., Billinghurst, R.C., Kawcak, C.E. and McIlwraith, C.W. (2008) Changes in synovial fluid and serum biomarkers with exercise and early osteoarthritis in horses. Osteoarthritis Cartilage 16, 1196-1204.

Frisbie, D.D., Mc Ilwraith, C.W., Arthur, R.M., Blea, J., Baker, V.A. and Billinghurst, R.C. (2010) Serum biomarker levels for musculoskeletal disease in two-and three-year-old racing Thoroughbred horses: A prospective study of 130 horses. Equine Veterinary Journal 42, 643-651.

Georgopoulos, S.P. and Parkin, T.D. (2016) Risk factors associated with fatal injuries in Thoroughbred racehorses competing in flat racing in the United States and Canada. J Am Vet Med Assoc 249, 931-939.

Georgopoulos, S.P. and Parkin, T.D. (2017) Risk factors for equine fractures in Thoroughbred flat racing in North America. Prev Vet Med 139, 99-104.

Graham, R.J.T.Y., Anderson, J.R., Phelan, M.M., Cillan-Garcia, E., Bladon, B.M. and Taylor, S.E. (2020) Metabolomic analysis of synovial fluid from Thoroughbred racehorses diagnosed with palmar osteochondral disease using magnetic resonance imaging. Equine Veterinary Journal 52, 384-390.

Heemskerk, V.H., Daemen, M.A.R.C. and Buurman, W.A. (1999) Insulin-like growth factor-1 (IGF-1) and growth hormone (GH) in immunity and inflammation. Cytokine & Growth Factor Reviews 10, 5-14.

Heleski, C., Stowe, C.J., Fiedler, J., Peterson, M.L., Brady, C., Wickens, C. and MacLeod, J.N. (2020) Thoroughbred Racehorse Welfare through the Lens of Social License to Operate—With an Emphasis on a U.S. Perspective. Sustainability 12.

Hernandez, J., Hawkins, D.L. and Scollay, M.C. (2001) Race-start characteristics and risk of catastrophic musculoskeletal injury in Thoroughbred racehorses. J Am Vet Med Assoc 218, 8386.

Hesse, K.L. and Verheyen, K.L. (2010) Associations between physiotherapy findings and subsequent diagnosis of belvic or hindlimb fracture in racing Thoroughbreds. Equine Vet J 42, 234-239.

Hill, A.E., Gardner, I.A., Carpenter, T.E. and Stover, S.M. (2004) Effects of injury to the suspensory apparatus, exercise, and horseshoe characteristics on the risk of lateral condylar fracture and suspensory apparatus failure in forelimbs of thoroughbred racehorses. Am J Vet Res 65, 1508-1517.

Hill, A.E., Gardner, I.A., Carpenter, T.E., Lee, C.M., Hitchens, P.L. and Stover, S.M. (2016) Prevalence, location and symmetry of noncatastrophic ligamentous suspensory apparatus lesions in California Thoroughbred racehorses, and association of these lesions with catastrophic injuries. Equine Vet J 48, 27-32.

Horohov, D.W., Sinatra, S.T., Chopra, R.K., Jankowitz, S., Betancourt, A. and Bloomer, R.J. (2012) The Effect of Exercise and Nutritional Supplementation on Proinflammatory Cytokine Expression in Young Racehorses During Training. Journal of Equine Veterinary Science 32, 805-815.

Huldani, Pattelongi, I., Massi, M.N., Idris, I., Bukhari, A., Wahyu Widodo, A.D. and Achmad, H. (2020) Research Reviews on Effect of Exercise on DAMP's, HMGB1, Proinflammatory Cytokines and Leukocytes. Systematic Reviews in Pharmacy 11, 306-312.

Johnson, B.J., Stover, S.M., Daft, B.M., Kinde, H., Read, D.H., Barr, B.C., Anderson, M., Moore, J., Woods, L., Stoltz, J. and Blanchard, P. (1994) Causes of death in racehorses over a 2 year period. Equine Veterinary Journal 26, 327-330.

Kane, A.J., Stover, S.M., Gardner, I.A., Bock, K.B., Case, J.T., Johnson, B.J., Anderson, M.L., Barr, B.C., Daft, B.M., Kinde, H., Larochelle, D., Moore, J., Mysore, J., Stoltz, J., Woods, L., Read, D.H. and Ardans, A.A. (1998) Hoof size, shape, and balance as possible risk factors for catastrophic musculoskeletal injury of Thoroughbred racehorses. Am J Vet Res 59, 1545-1552.

Kane, A.J., Stover, S.M., Gardner, I.A., Case, J.T., Johnson, B.J., Read, D.H. and Ardans, A.A. (1996) Horseshoe characteristics as possible risk factors for fatal musculoskeletal injury of thoroughbred racehorses. Am J Vet Res 57, 1147-1152.

Kristoffersen, M., Parkin, T.D. and Singer, E.R. (2010) Catastrophic biaxial proximal sesamoid bone fractures in UK Thoroughbred races (1999-2004): horse characteristics and racing history. Equine Vet J 42, 420-424.

Lehnhard, R., Adams, A., Betancourt, A., Horohov, D., Liburt, N., Streltsova, J., Franke, W. and McKeever, K. (2010) Phenylbutazone blocks the cytokine response following a high-intensity incremental exercise challenge in horses. Comparative Exercise Physiology 7, 103-108.

(56) References Cited

PUBLICATIONS

Liburt, N.R., Adams, A.A., Betancourt, A., Horohov, D.W. and Mckeever, K.H. (2010) Exercise-induced increases in inflammatory cytokines in muscle and blood of horses. Equine Vet J Suppl 42, 280-288.

Lieu, S., Hansen, E., Dedini, R., Behonick, D., Werb, Z., Miclau, T., Marcucio, R. and Colnot, C. (2011) Impaired remodeling phase of fracture repair in the absence of matrix metalloproteinase-2. Disease Models & Mechanisms 4, 203.

Livak, K.J. and Schmittgen, T.D. (2001) Analysis of Relative Gene Expression Data Using Real-Time Quantitative PCR and the 2-ΔΔCT Method. Methods (San Diego, Calif.) 25, 402-408.

Loughridge, A.B., Hess, A.M., Parkin, T.D. and Kawcak, C.E. (2017) Qualitative assessment of bone density at the distal articulating surface of the third metacarpal in Thoroughbred racehorses with and without condylar fracture. Equine Vet J 49, 172-177.

Majidinia, M., Sadeghpour, A. and Yousefi, B. (2018) The roles of signaling pathways in bone repair and regeneration. Journal of Cellular Physiology 233, 2937-2948.

Manfredi, A.A., Capobianco, A., Bianchi, M.E. and Rovere-Querini, P. (2009) Regulation of Dendritic- and T-Cell Fate by Injury-Associated Endogenous Signals. 29, 69-86.

Martig, S., Chen, W., Lee, P.V. and Whitton, R.C. (2014) Bone fatigue and its implications for injuries in racehorses. Equine Vet J 46, 408-415.

Nieman, D.C. and Pedersen, B.K. (1999) Exercise and Immune Function. Sports Medicine 27, 7380.

Nieman, D.C., Henson, D.A., Davis, J.M., Dumke, C.L., Utter, A.C., Murphy, E.A., Pearce, S., Gojanovich, G., McAnulty, S.R. and McAnulty, L.S. (2006) Blood leukocyte mRNA expression for IL-10, IL-1Ra, and IL-8, but not IL-6, increases after exercise. J Interferon Cytokine Res 26, 668674.

O'Brien, T., Baker, T.A., Brounts, S.H., Sample, S.J., Markel, M.D., Scollay, M.C., Marquis, P. and Muir, P. (2011) Detection of articular pathology of the distal aspect of the third metacarpal bone in thoroughbred racehorses: comparison of radiography, computed tomography and magnetic resonance imaging. Vet Surg 40, 942-951.

Ostrowski, K., Rohde, T., Asp, S., Schjerling, P. and Pedersen, B.K. (1999) Pro- and anti-inflammatory cytokine balance in strenuous exercise in humans. The Journal of Physiology 515, 287-291.

Equine Injury Database, The Jockey Club, 2021. pp. 1-4.

Page, A.E., Adam, E., Stewart, J.C., Gonzales, C., Barker, V. and Horohov, D.W. (2020) Alterations of peripheral gene expression in response to lipopolysaccharide-induced synovitis as a model for inflammation in horses. Veterinary Immunology and Immunopathology 225, 110058.

Page, A.E., Stewart, J.C., Fielding, C.L. and Horohov, D.W. (2019) The effect of a 160-kilometer competitive endurance ride on inflammatory marker mRNA expression in horses. Journal of Equine Veterinary Science 79, 45-49.

Page, A.E., Stewart, J.C., Holland, R.E. and Horohov, D.W. (2017) The Impact of Training Regimen on the Inflammatory Response to Exercise in 2-Year-Old Thoroughbreds. Journal of Equine Veterinary Science 58, 78-83.

Page, A.E., Stewart, J.C., Scollay, M.C. and Horohov, D.W. (2019) Comparison of pre-race inflammatory marker mRNA expression with race-related parameters in Thoroughbreds. Comparative Exercise Physiology 16, 101-106.

Parkin, T.D. (2007) Epidemiology of training and racing injuries. Equine Vet J 39, 466-469.

Parkin, T.D. (2008) Epidemiology of racetrack injuries in racehorses. The Veterinary clinics of North America. Equine practice 24, 1-19.

Parkin, T.D., Clegg, P.D., French, N.P., Proudman, C.J., Riggs, C.M., Singer, E.R., Webbon, P.M. and Morgan, K.L. (2004) Horse-level risk factors for fatal distal limb fracture in racing Thoroughbreds in the UK. Equine Vet J 36, 513-519.

Parkin, T.D., Clegg, P.D., French, N.P., Proudman, C.J., Riggs, C.M., Singer, E.R., Webbon, P.M. and Morgan, K.L. (2006) Catastrophic fracture of the lateral condyle of the third metacarpus/metatarsus in UK racehorses—fracture descriptions and pre-existing pathology. Vet J 171, 157-165.

Peloso, J.G., Mundy, G.D. and Cohen, N.D. (1994) Prevalence of, and factors associated with, musculoskeletal racing injuries of thoroughbreds. J Am Vet Med Assoc 204, 620-626.

Peloso, J.G., Vogler, J.B., 3rd, Cohen, N.D., Marquis, P. and Hilt, L. (2015) Association of catastrophic biaxial fracture of the proximal sesamoid bones with bony changes of the metacarpophalangeal joint identified by standing magnetic resonance imaging in cadaveric forelimbs of Thoroughbred racehorses. J Am Vet Med Assoc 246, 661-673.

Perkins, N.R., Reid, S.W. and Morris, R.S. (2005) Risk factors for musculoskeletal injuries of the lower limbs in Thoroughbred racehorses in New Zealand. N Z Vet J 53, 171-183.

Philippou, A., Bogdanis, G., Maridaki, M., Halapas, A., Sourla, A. and Koutsilieris, M. (2009) Systemic cytokine response following exercise-induced muscle damage in humans. Clinical chemistry and laboratory medicine 47, 777-782.

Riggs, C.M., Whitehouse, G.H. and Boyde, A. (1999) Pathology of the distal condyles of the third metacarpal and third metatarsal bones of the horse. Equine Vet J 31, 140-148.

Scollay, M.C. (2017) Autopsy of the racehorse: the regulator's perspective. Journal of veterinary diagnostic investigation : official publication of the American Association of Veterinary Laboratory Diagnosticians, Inc 29, 383-384.

Smith, L.L. (2004) Tissue trauma: the underlying cause of overtraining syndrome? J Strength Cond Res 18, 185-193.

Spriet, M., Espinosa-Mur, P., Cissell, D.D., Phillips, K.L., Arino-Estrada, G., Beylin, D., Stepanov, P., Katzman, S.A., Galuppo, L.D., Garcia-Nolen, T., Murphy, B. and Stover, S.M. (2019) 18F-sodium fluoride positron emission tomography of the racing Thoroughbred fetlock: Validation and comparison with other imaging modalities in nine horses. Equine Veterinary Journal 51, 375-383.

Swift, J. and G.M. Coruzzi, A matter of time—How transient transcription factor interactions create dynamic gene regulatory networks.Biochimica et biophysica acta. Gene regulatory mechanisms, 2017. 1860(1): p. 75-83.

Tozaki, T., Kusano, K., Ishikawa, Y., Kushiro, A., Nomura, M., Kikuchi, M., Kakoi, H., Hirota, K., Miyake, T., Hill, E.W. and Nagata, S. (2020) A candidate-SNP retrospective cohort study for fracture risk in Japanese Thoroughbred racehorses. Animal Genetics 51, 43-50.

Tranquille, C.A., Murray, R.C. and Parkin, T.D. (2017) Can we use subchondral bone thickness on high-field magnetic resonance images to identify Thoroughbred racehorses at risk of catastrophic lateral condylar fracture? Equine Vet J 49, 167-171.

Tranquille, C.A., Parkin, T.D. and Murray, R.C. (2012) Magnetic resonance imaging-detected adaptation and pathology in the distal condyles of the third metacarpus, associated with lateral condylar fracture in Thoroughbred racehorses. Equine Vet J 44, 699-706.

Trope, G.D., Ghasem-Zadeh, A., Anderson, G.A., Mackie, E.J. and Whitton, R.C. (2015) Can high-resolution peripheral quantitative computed tomography imaging of subchondral and cortical bone predict condylar fracture in Thoroughbred racehorses? Equine Vet J 47, 428-432.

Turlo, A.J., Cywinska, A. and Frisbie, D.D. (2019) Revisiting predictive biomarkers of musculoskeletal injury in thoroughbred racehorses: longitudinal study in polish population. BMC veterinary research 15, 66.

Vallance, S.A., Entwistle, R.C., Hitchens, P.L., Gardner, I.A. and Stover, S.M. (2013) Case-control study of high-speed exercise history of Thoroughbred and Quarter Horse racehorses that died related to a complete scapular fracture. Equine Vet J 45, 284-292.

Verheyen, K.L., Price, J.S. and Wood, J.L. (2007) Fracture rate in Thoroughbred racehorses is affected by dam age and parity. Vet J 174, 295-301.

Vezzoli, M., Castellani, P., Corna, G., Castiglioni, A., Bosurgi, L., Monno, A., Brunelli, S., Manfredi, A.A., Rubartelli, A. and Rovere-Querini, P. (2011) High-Mobility Group Box 1 Release and Redox Regulation Accompany Regeneration and Remodeling of Skeletal Muscle. Antioxidants & Redox Signaling 15, 2161-2174.

(56) References Cited

PUBLICATIONS

Vick, M.M., Murphy, B.A., Sessions, D.R., Reedy, S.E., Kennedy, E.L., Horohov, D.W., Cook, R.F. and Fitzgerald, B.P. (2008) Effects of systemic inflammation on insulin sensitivity in horses and inflammatory cytokine expression in adipose tissue. American Journal of Veterinary Research 69, 130-139.

Walsh, N.P., Gleeson, M., Shephard, R.J., Gleeson, M., Woods, J.A., Bishop, N.C., Fleshner, M., Green, C., Pedersen, B.K., Hoffman-Goetz, L., Rogers, C.J., Northoff, H., Abbasi, A. and Simon, P. (2011) Position statement part one: Immune function and exercise. Exercise immunology review 17, 6-63.

Welsh, C.E., Lewis, T.W., Blott, S.C., Mellor, D.J., Stirk, A.J. and Parkin, T.D. (2014) Estimates of genetic parameters of distal limb fracture and superficial digital flexor tendon injury in UK Thoroughbred racehorses. Vet J 200, 253-256.

Davidson, Elizabeth J. "Controlled Exercise in Equine Rehabilitation." Veterinary Clinics: Equine Practice 32.1 (2016): 159-165.

Pleasant, R. Scott, et al. "Stress Reactions and Stress Fractures of the Proximal Palmer Aspect of the Third Metacarpal Bone in Horses: 58 Cases (1980-1990)." Journal of the American Veterinary Medical Association 201.12 (1992): 1918-1923.

Arnold, C. E., et al. "Conservative management of 17 horses with nonarticular fractures of the tibial tuberosity." Equine veterinary journal 35.2 (2003): 202-206.

Hinchcliff, Kenneth W., et al., "Equine Sports Medicine and Surgery: Basic Clinical Sciences of the Equine Athlete" (2004) teaches "Regardless of the level of rehabilitation undertaken, initial management involves cessation of training and aggressive anti-inflammatory therapy." pp. 1058, 1059.

\* cited by examiner

DETECTION OF EXPRESSION OF MARKERS USEFUL FOR PREDICTING RISK OF CATASTROPHIC INJURIES IN ATHLETIC ANIMALS

RELATED APPLICATIONS

This application claims the benefit of U.S. Provisional Application Ser. No. 62/988,280 filed Mar. 11, 2020 and U.S. Provisional Application Ser. No. 63/119,498 filed on Nov. 30, 2020, the entire disclosure of each of which is incorporated herein by this reference.

TECHNICAL FIELD

The presently-disclosed subject matter generally relates to gene expression detection in biological samples from animals, such as non-human athletic animals. More specifically, embodiments of the present disclosure relate to methods for identifying risk of catastrophic injury in non-human athletic animals based on gene expression within biological samples obtained from such animals, which can be determined using mRNA expression analysis.

BACKGROUND

Despite the work of numerous groups detailing a multitude of risk-factors associated with catastrophic injuries (CI's) in Thoroughbred racehorses across the world,[1-16] the ability to reduce the number of CI's in North America remains a significant challenge.[17] It has been established that many CI's occur in limbs with underlying or pre-existing pathology,[18-25] leading to the theory that acute injury is due to the accumulation of mild to moderate damage over time at a rate that exceeds the healing capacity of the affected tissues.[6] Thus, earlier detection of this damage followed by corrective action could reduce the incidence of fatal and/or career-ending injuries.[26]

Advanced imaging techniques, such as computed tomography, magnetic resonance imaging, and positron emission tomography, have all been proposed as a possible means for detecting impending CI's.[19, 27-30] With a recent review providing information specifically on imaging of the jfetlock,[31] more work is urgently needed in this area to better understand and identify risk factor-associated changes. Unfortunately, these approaches may be cost prohibitive if used on a regular, screening basis and/or they may require general anesthesia.

Alternatively, others have suggested using genetic screening or predictive modeling to identify those horses at greatest risk for CI's,[4, 32-34] though the utility of these approaches have yet to be proven. While the detection of biomarkers for equine injuries has also been explored,[35-39] their use has not been widely adopted, despite some reported success.[40, 41]

This overall shift from retrospective examination to a more proactive application of research signals a positive move towards catastrophic injury prevention, especially given recent headlines and negative attention regarding catastrophic injuries in North America.[42]

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permuations of these embodiments. The summary is merely exemplary of the numerous varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations.

The presently-disclosed subject matter includes methods which include obtaining a biological sample from an animal, such as a non-human athletic animal, and detecting expression of a gene or a combination of genes within the biological sample. In particular, the presently-disclosed subject matter includes methods of detecting, within the biological sample, the expression of one or more genes which may serve useful as a potential biomarker for identifying when the animal is at an increased risk of experiencing a catastrophic injury (CI).

In some embodiments of the methods of the present disclosure, the gene(s) detected within the biological sample, which may serve as a potential biomarker indicative of increased risk for CI, includes one or more genes selected from the group consisting of interleukin 1 receptor antagonist (IL1RN), insulin-like growth factor (IGF-1), matrix metallopeptidase 2 (MMP2), arachidonate 5-Lipoxygenase Activating Protein (ALOX5AP), cluster of differentiation 14 (CD14), interleukin 1 beta (IL-1β), interleukin 6 (IL-6), interleukin 8 (IL-8), interleukin 10 (IL-10), matrix metallopeptidase 1 (MMP1), prostaglandin-endoperoxide synthase 2 (PTGS2), toll-like receptor 4 (TLR4), tumor necrosis factor alpha (TNFα), tumor necrosis factor receptor superfamily member 13B (TNFSF13B), and vascular endothelial growth factor A (VEGFA). In some embodiments, the gene(s) detected within the biological sample is selected from the group consisting of IL1RN, IGF-1, MMP2, ALOX5AP, and IL-6. In some embodiments, the genes detected within the biological sample is a combination of two or more genes selected form the group consisting of IL1RN, IGF-1, MMP2, ALOX5AP, and IL-6. In some embodiments, the combination of genes detected within the biological sample includes at least one of IL1RN, IGF-1, and MMP2.

In some embodiments, the methods of the present disclosure may further comprise identifying the animal from which the biological sample was taken as having a risk of a CI or excluding the animal as having a risk of a CI based on the expression of the one or more genes detected within the biological sample. In some embodiments, the expression of each gene is identified by comparing the expression of the gene within the biological sample to a baseline calibrator or non-injured population of animals. In some embodiments, changes in the expression of each gene are identified by obtaining a second biological sample from the animal at a time point subsequent to when the first biological sample was obtained and comparing the two samples.

In some embodiments, the biological sample is obtained from whole peripheral blood of the animal. In some embodiments, the biological sample is buffy coat fraction of the whole peripheral blood. In some embodiments, the biological sample is plasma or serum from the whole peripheral blood. In some embodiments, the biological sample is taken from a horse, such as a Thoroughbred racehorse.

In the methods of the present disclosure, detecting the expression of one or more genes serving as a potential biomarker for CI detection is preferably achieved via mRNA expression analysis. In this regard, the expression level of the one or more genes may be determined by the levels of mRNA corresponding to the one or more genes within the biological sample. Certain methods of the present disclosure may thus further comprise extracting mRNA from the biological sample. In some embodiments, mRNA levels corresponding to the one or more genes may be determined by using quantitative polymerase chain reaction (qPCR) to measure cDNA of the mRNA. By virtue of utilizing biological samples taken from the animal and mRNA expression analysis, risk of CI can thus be detected in a more economical, efficient, and non-invasive manner than techniques currently employed within the art.

Further provided in the presently-disclosed subject matter is a kit for detecting gene expression in a biological sample from an animal, such as a non-human athletic animal. The kit includes a primer specific for one or more of the genes referred to herein. In some embodiments, the kit includes a primer specific for each of at least two genes selected from the group consisting of IL1RN, IGF-1, MMP2, ALOX5AP, and IL-6.

BRIEF DESCRIPTION OF THE DRAWINGS

The presently-disclosed subject matter will be better understood, and features, aspects, and advantages other than those set forth above will become apparent when consideration is given to the following detailed description thereof. Such detailed description makes reference to the following drawings wherein:

In FIG. 1, * denotes a significant difference (p<0.05) when compared to the other two groups.

In FIG. 2, * denotes a significant difference (p<0.05) when compared to the other two groups.

In FIG. 3, * denotes a significant difference (p<0.05) when compared to the other two groups.

In FIG. 4, * denotes a significant difference (p<0.05) when compared to the other two groups.

In FIG. 5, * denotes a significant difference (p<0.05) between the specific injury type and non-injured horses.

In FIG. 6, * denotes a significant difference (p<0.05) between the specific injury type and non-injured horses.

In FIG. 7, * denotes a significant difference (p<0.05) between the specific injury type and non-injured horses.

In FIG. 8, * denotes a significant difference (p<0.05) between the specific injury type and non-injured horses.

In FIG. 11, * denotes a significant difference (P<0.05) in expression between paired samples.

In FIG. 13A, * denotes a significant difference (P<0.05) when compared to the non-injured control horses.

In FIG. 13B, * denotes a significant difference (P<0.05) when compared to the non-injured control horses.

In FIG. 13C, * denotes a significant difference (P<0.05) when compared to the non-injured control horses.

BRIEF DESCRIPTION OF THE SEQUENCE LISTING

Figure 1:
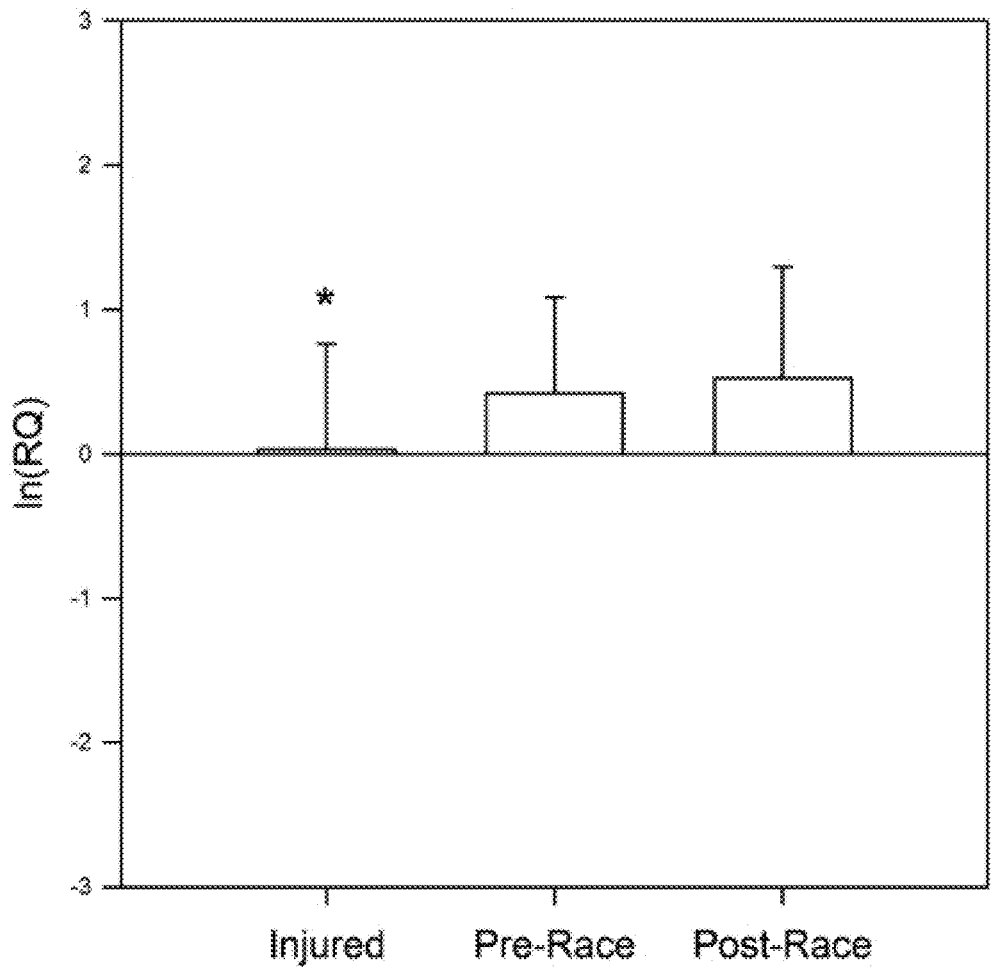
FIG. 1 shows a comparison of mRNA expression of ALOX5AP expression (ln(Relative Quantity)) between catastrophically injured horses and non-injured horses sampled either pre-race or post-race.

SEQ ID NO: 1 is a nucleotide sequence which corresponds to and allows the detection of ALOX5AP mRNA during qPCR.

SEQ ID NO: 2 is an amino acid sequence encoded by ALOX5AP mRNA corresponding to SEQ ID NO: 1.

SEQ ID NO: 3 is a nucleotide sequence which corresponds to and allows the detection of IGF-1 mRNA during qPCR.

SEQ ID NO: 4 is an amino acid sequence encoded by IGF-1 mRNA corresponding to SEQ ID NO: 3.

SEQ ID NO: 5 is a nucleotide sequence which corresponds to and allows the detection of IL-6 mRNA during qPCR.

SEQ ID NO: 6 is an amino acid sequence encoded by IL-6 mRNA corresponding to SEQ ID NO: 5.

SEQ ID NO: 7 is a nucleotide sequence which corresponds to and allows detection of MMP2 mRNA during qPCR.

SEQ ID NO: 8 is an amino acid sequence encoded by MMP2 mRNA corresponding to SEQ ID NO: 7.

SEQ ID NO: 9 is a nucleotide sequence which corresponds to and allows detection of IL1RN mRNA during qPCR.

SEQ ID NO: 10 is an amino acid sequence encoded by IL1RN mRNA corresponding to SEQ ID NO: 9.

SEQ ID NO: 11 is a nucleotide sequence which corresponds to and allows detection of MMP9 mRNA during qPCR.

SEQ ID NO: 12 is an amino acid sequence encoded by MMP9 mRNA corresponding to SEQ ID NO: 11.

SEQ ID NO: 13 is a nucleotide sequence which corresponds to and allows detection of VEGFA mRNA during qPCR.

SEQ ID NO: 14 is an amino acid sequence encoded by VEGFA mRNA corresponding to SEQ ID NO: 13.

The above-identified sequences are provided within the text file entitled "UKRF 2405 NonProvisional Sequence Listing ST25" (29 Kilobytes) created on Mar. 11, 2021 filed with the present disclosure, the entire disclosure of which is incorporated herein by this reference.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter is illustrated by specific but non-limiting examples throughout this description. The examples may include compilations of data that are representative of data gathered at various times during the course of development and experimentation related to the present invention(s). Each example is provided by way of explanation of the present disclosure and is not a limitation thereon. In fact, it will be apparent to those skilled in the art that various modifications and variations can be made to the teachings of the present disclosure without departing from the scope of the disclosure. For instance, features illustrated or described as part of one embodiment can be used with another embodiment to yield a still further embodiment.

All combinations of methods or process steps as used herein can be performed in any order, unless otherwise specified or clearly implied to the contrary by the context in which the referenced combination is made.

While the following terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs.

All patents, patent applications, published applications and publications, GenBank sequences, databases, web-sites and other published materials referred throughout the entire disclosure herein, unless noted otherwise, are incorporated by reference in their entirety.

Where reference is made to a URL or other such identifier or address, it is understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Some of the polynucleotide and polypeptide sequences disclosed herein are cross-referenced to GENBANK®/GENPEPT® accession numbers. The sequences cross-referenced in the GENBANK®/GENPEPT® database are expressly incorporated by reference as are equivalent and related sequences present in GENBANK®/GENPEPT® or other public databases, such as National Center for Biotechnology Information (NCBI) databases. Also expressly incorporated herein by reference are all annotations present in the GENBANK®/GENPEPT® database associated with the sequences disclosed herein. Unless otherwise indicated or apparent, the references to the GENBANK®/GENPEPT® database are references to the most recent version of the database as of the filing date of this Application.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, in some embodiments ±0.1%, in some embodiments ±0.01%, and in some embodiments ±0.001% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

As used herein, the term "animal" refers to vertebrate animal that is not a human, and preferably refers to a mammal that is not a human. For example, the term animal can refer, in some embodiments, to a horse, a camel, a dog, an elephant, a pig, a goat, a donkey, and other non-human animals. The term is inclusive of animals of different breeds, for example, a horse is inclusive of a Thoroughbred, Standardbred, Saddlebred, and other breeds of horses, including those classified as cold bloods, warm bloods, and hot bloods.

The term "athletic animal" refers to an animal that participates in an animal sporting event. In some cases, participating in an animal sporting event involves selective breeding, training to prepare for a sporting event, and participation in a sporting event. In some cases, a human is participating with the animal in the animal sporting event. In some cases, a human is not participating with the animal in the animal sporting event. Examples of sporting events include, but are not limited to, racing, polo, jousting, showing, eventing, jumping, dressage, obstacle course, and agility competition.

As used herein, the term "catastrophic injury" refers to a fatal or non-fatal musculoskeletal injury sustained by an athletic animal during racing or training that results in an acute lameness. Such injuries include, but are not limited to, condylar fractures (fractures of the lateral or medial condyle of the third metacarpal or metatarsal bone, also called the cannon bone); fractures of the proximal sesamoid bones, whether involving one or more proximal sesamoid bones; fractures in one or more bones of the carpus (the knee) or tarsus (the hock); rupture of the suspensory apparatus or other tendons or ligaments; P1 (long pastern bone) or P2 (short pastern bone) fractures/sagittal fractures (or any fracture of the distal limb); and any other bony fractures, including those of the scapula, tibia, humerus, pelvis, femur, or stifle joint.

An alternative, less-invasive approach for identifying horses at risk for injury based on research with human athletes regarding exercise-induced, pro-inflammatory cytokine production and its modulation during training[43-45] is contemplated herein. It is believed that exercise-induced inflammation involving high volume/intensity training produces muscle and/or bone trauma resulting in the release of damage associated molecular patterns (DAMPs).[46] These molecules are released by cells undergoing necrosis and act as endogenous danger signals to promote an inflammatory response.[47] DAMPs bind to receptors on the surface of dendritic cells, monocytes, macrophages, and other cells leading to the production of pro-inflammatory cytokines such as tumor necrosis factor-alpha (TNF-α), interleukin (IL)-1β, and IL-6.[48]

Post-exercise increases in inflammatory markers are known to occur within several hours of exercise in humans,[49, 50] and work performed in horses has shown that some of the same markers (TNF-α and IL-1β) exhibit increased expression in circulating leukocytes two or more hours after the completion of exercise.[51-54] Effective exercise conditioning, on the other hand, leads to a decrease in this inflammatory response and the adoption of an anti-inflammatory state.[53-55]

Therefore, it is contemplated that, prior to or during the early post-race period, appropriately conditioned, healthy horses will exhibit reduced expression of inflammatory markers in their peripheral blood. By contrast and based upon the knowledge that CI's occur in limbs with preexisting damage, increased inflammation could be indicative of impending injury or an increased risk for injury.[56]

The present inventors contemplated that athletic animals, such as Thoroughbred racehorses, with a catastrophic injury during training or racing would demonstrate increased inflammatory gene expression at the time of their injury when compared to non-injured control horses. This is based on the known timing of inflammatory mRNA changes in response to exercise[51, 53] and localized inflammation,[57] such that samples collected immediately post-injury/post-race will represent the pre-race inflammatory status of the individual horses.

The presently-disclosed subject matter includes a method of detecting gene expression in a biological sample from a non-human athletic animal, which involves obtaining a biological sample from the animal and detecting in the biological sample the expression of at least one gene selected from the group consisting of interleukin 1 receptor antagonist (IL1RN), insulin-like growth factor (IGF-1), matrix metallopeptidase 2 (MMP2), arachidonate 5-Lipoxygenase Activating Protein (ALOX5AP), and interleukin 6 (IL-6). In some embodiments, a combination of two or more genes selected from the group consisting of IL1RN, IGF-1, MMP2, ALOX5AP, and IL-6 are detected within the biological sample. In some embodiments, the combination of two or more genes detected in the biological sample includes at least one of IL1RN, IGF-1, and MMP2. In one such embodiment, the combination of two or more genes detected in the biological sample further includes at least one additional gene selected from the group consisting of ALOX5AP, cluster of differentiation 14 (CD14), interleukin 1 beta (IL-1β), IL-6, interleukin 8 (IL-8), interleukin 10 (IL-10), matrix metallopeptidase 1 (MMP1), prostaglandin-endoperoxide synthase 2 (PTGS2), toll-like receptor 4 (TLR4), tumor necrosis factor alpha (TNFα), tumor necrosis factor receptor superfamily member 13B (TNFSF13B), and vascular endothelial growth factor A (VEGFA). In some embodiments, the combination of two or more genes detected in the biological sample includes IL1RN, IGF-1, and MMP2.

In some embodiments, the method of detecting gene expression in a biological sample from a non-human athletic animal, further involves: obtaining an additional (or "second") biological sample from the animal at a time point subsequent to when the initial (or "first") biological sample was obtained; detecting in the second biological sample the expression of the same gene(s) detected in the first biological sample; and identifying changes in expression of such gene(s) by comparing the second biological sample to the first biological sample. In this regard, depending on the gene(s) selected for detection in the first biological sample, at least one of IL1RN, IGF-1, MMP2, ALOX5AP, and IL-6 is detected in the second biological sample. In some embodiments, CD14, IL-1β, IL-8, IL-10, MMP1, PTGS2, TLR4, TNFα, TNFSF13B, and/or VEGFA may also be detected in the second biological sample. In some embodiments, more than one additional biological sample may be obtained from the animal at a time point subsequent to when the first biological was obtained and compared to the first biological sample to identify changes in gene expression. In this regard, in some embodiments, the method may include detecting changes in gene expression in the animal over various periods of time.

The presently-disclosed subject matter further includes a method of detecting risk for a catastrophic injury in a non-human athletic animal, which involves obtaining a biological sample from the animal; detecting expression of at least one gene in the biological sample; and identifying a risk associated with the animal based on expression of the at least one gene. In some embodiments, the at least one gene detected in the biological sample is selected from the group consisting of: IL1RN, IGF-1, MMP2, ALOX5AP, IL-6, CD14, IL-1β, IL-6, IL-8, IL-10, MMP1, PTGS2, TLR4, TNFα, TNFSF13B, and VEGFA. In some embodiments, the at least one gene detected in the biological sample is selected from the group consisting of: IL1RN, IGF-1, MMP2, ALOX5AP, and IL-6. In some embodiments, the at least one gene detected in the biological sample is selected from the group consisting of: IL1RN, IGF-1, and MMP2.

In methods disclosed herein, which involve detecting or diagnosing a risk for a catastrophic injury in a non-human athletic animal, a risk of catastrophic injury can be associated with the animal when differential expression shows the gene(s) selected for detection in biological samples exhibiting increased or decreased expression levels. For example, in some embodiments, the animal can be identified as having a risk of catastrophic injury when the gene(s) selected for detection exhibit a decreased or increased expression of the genes as identified in the second column of Table 1. For another example, in some embodiments the animal can be excluded from having a risk of catastrophic injury when the biological sample has substantially the same expression, or an increased or decreased expression of the genes as identified in the third column of the following Table 1.

TABLE 1

Risk of injury as related to gene expression.

| | Identify a risk when differential expression shows: | Exclude a risk when differential expression shows: |
|---|---|---|
| interleukin 1 receptor antagonist (IL1RN) | Decrease | Increase |
| insulin-like growth factor (IGF-1) | Increase | Decrease |
| matrix metallopeptidase 2 (MMP2) | Increase | Decrease |
| arachidonate 5-Lipoxygenase Activating Protein (ALOX5AP) | Decrease | Increase |
| interleukin 1 beta (IL-1β) | Decrease | Increase |
| interleukin 6 (IL-6) | Decrease | Increase |
| prostaglandin-endoperoxide synthase 2 (PTGS2) | Decrease | Increase |
| vascular endothelial growth factor A (VEGFA) | Decrease | Increase |
| cluster of differentiation 14 (CD14) | Increase | Decrease |
| interleukin 8 (IL-8) | Increase | Decrease |
| interleukin 10 (IL-10) | Increase | Decrease |
| matrix metallopeptidase 1 (MMP1) | Increase | Decrease |
| toll-like receptor 4 (TLR4) | Increase | Decrease |
| tumor necrosis factor alpha (TNFα) | Increase | Decrease |
| tumor necrosis factor receptor superfamily member 13B (TNFSF13B) | Increase | Decrease |

The differential expression can be assessed relative to a baseline calibrator or a non-injured population of animals. The "baseline calibrator" for each gene can be the average expression level of that gene in a group of sedentary animals of the same species as the animal from which the biological sample was obtained. The expression in a non-injured population of animals for each gene can be the average expression level of that gene in a group of non-injured animals of the same species as the animal from which the biological sample was obtained.

In embodiments of the methods described herein, when a risk has been identified, the methods can further involve providing treatment to the animal. In some embodiments, treatment of the animal includes implementing advanced diagnostics to localize potential injury locations. In some embodiments treatment of the animal includes suspending the animal from high-intensity exercise. In some embodiments, treatment of the animal may persist until such time as it is determined that the animal is no longer at risk.

In this regard, in some embodiments, the method of detecting risk for a catastrophic injury in a non-human athletic animal involves obtaining an additional (or "second") biological sample from the animal at a time point subsequent to when the initial (or "first") biological sample was obtained; detecting in the second biological sample expression of the same gene(s) detected in the first biological sample; and identifying changes in expression of such gene(s) by comparing the second biological sample to the first biological sample. In some embodiments, changes in the expression of the at least one gene in the second biological sample as compared to the first biological sample are identified. Such changes can be indicative of a change in the risk profile for the animal. In this regard, depending on the gene(s) selected for detection in the first biological sample, at least one of IL1RN, IGF-1, MMP2, ALOX5AP, and IL-6 is detected in the second biological sample. In some embodiments, CD14, IL-1β, IL-8, IL-10, MMP1, PTGS2, TLR4, TNFα, TNFSF13B, and/or VEGFA may be detected in the second biological sample. In some embodiments, more than one additional biological sample may be obtained from the animal at a time point subsequent to when the first biological was obtained and compared to the first biological sample to identify changes in gene expression. In this regard, in some embodiments, the method may include detecting changes in gene expression in the animal over various periods of time.

In some embodiments, the method of detecting risk for a catastrophic injury in a non-human athletic animal involves identifying the animal as having a continued risk and/or having developed a risk when the second biological sample has a decreased or an increased expression relative to a baseline calibrator or a non-injured population of animals for one or more genes as identified in the second column of Table 1, or excluding the animal from having a risk and/or identifying the animal as no longer having a risk when the second biological sample has a decreased or an increased expression relative to a baseline calibrator or a non-injured population of animals for one or more genes as identified in the third column of Table 1.

As noted hereinabove, the methods disclosed herein make use of a biological sample obtained from the animal. Because the methods involve detecting expression of particular genes, the biological sample should be selected to allow for such detection. For example, the biological sample can be selected due to its inherent inclusion of expressed gene products, such as mRNA. In this regard, whole peripheral blood can be selected and used as the biological sample in some embodiments of the methods disclosed herein. Other examples of biological samples which may be selected and used as the biological sample included in the methods disclosed herein include, but are not limited to, plasma, serum, and buffy coat fraction of blood.

In some embodiments of the methods disclosed herein, the method of the presently-disclosed subject matter, a biological sample is obtained from the animal within 1, 2, 3, 4, 5, 6, 7, 8, 9, or 10 days from when the animal is scheduled for training or a race.

In some embodiments of the presently-disclosed subject matter, the method of detecting risk for a catastrophic injury in a non-human athletic animal can further involve determining at least one additional risk factor, including, but not limited to, age of the animal, age of the animal at first race, sex of the animal, distance of first race, distance of most-recent race, average distance of all races, type and condition of track surface for first race, type and condition of track surface for most recent race, most common type and condition of track surface for all races, class of race of first race, class of race of most-recent race, most common class of race, and total number of races.

Some embodiments of the presently-disclosed subject matter also involve extracting mRNA from the biological sample. In some embodiments, the method also involves measuring in the extracted mRNA the levels of mRNA corresponding to the gene(s) selected for detection in the biological sample. In some embodiments, the method also involves using quantitative polymerase chain reaction (qPCR) to measure the mRNA by measuring cDNA of the mRNA.

The presently-disclosed subject matter further includes a kit comprising a primer specific for each of one or more of the genes as disclosed herein. In some embodiments, the kit comprises a primer specific for each of at least two genes selected from the group consisting of IL1RN, IGF-1, MMP2, ALOX5AP, and IL-6. In some embodiments, the kit comprises a primer specific for each of at least two genes selected from the group consisting of ILRN, IGF-1, and MMP2.

The presently-disclosed subject matter is further illustrated by the following specific but non-limiting examples. The following examples may include compilations of data that are representative of data gathered at various times during the course of development and experimentation related to the present invention.

EXAMPLES

The following Examples are based on prospective cohort studies conducted during a study period spanning from September 2017 to January 2020 which focused on the use of mRNA expression analysis to determine select gene expression in catastrophically injured Thoroughbred racehorses. In the studies, biological samples were taken from Thoroughbred horses across five different racing jurisdictions across the United States. As further described below, samples collected from injured horses were collected immediately post-injury and prior to any potential injury-induced changes in mRNA expression and any genes where expression was significantly affected by exercise alone were excluded from further data analysis. In this regard, the mRNA expression results of the samples reviewed during the data analysis portion of the studies represented transcriptional activity of the genes selected for study.

Example 1

Materials and Methods

Horses, Sample Collection, and Inclusion Criteria

Horses eligible for inclusion in this study were those Thoroughbreds entered into any race in a participating jurisdiction (n=5) during the study period. In total, 645 horses were included in the data analysis, of which 100 were catastrophically injured (CI) horses and 545 were non-injured. Of the non-injured horses, 336 were pre-race horses, and 209 were post-race horses.

The biological samples taken from the horses consisted of 3 mL of peripheral blood collected into a single Tempus™ tube (Applied Biosystems, Inc., Foster City, CA). Samples from CI horses were collected as soon as possible post-injury, either prior to or immediately after euthanasia, but within 30 minutes post-injury. From the same race, one or more horses held for post-race drug testing were also sampled within 45 minutes of the race's conclusion (post-race controls). Additionally, a number of post-race samples from races without CI's were collected within this same timeframe. Lastly, samples were collected by participating jurisdictions during pre-race total carbon dioxide ($TCO_2$) testing (pre-race controls). The investigators were blinded to the status of sampled horses (e.g. injured, pre-race, or post-race) by the participating jurisdictions until RNA isolation and quantitative polymerase chain reaction (qPCR) was performed.

Following identification of the blinded samples, public records (www.equibase.com, Equibase Company, LLC, Lexington, Ky.) were used to capture data on each sampled horse. Data collected included: sex, age, race type, and whether the horse raced again within three months of the sampled race. For injured horses, the race narrative was examined to identify any possible confounding factors related to the injury. As such, injured horses were excluded from the data analysis if they were noted to have clipped heels and fallen, been bumped and fallen, or experienced sudden death. Necropsy results, where available, were obtained and utilized to categorize the type of musculoskeletal injury that was sustained (e.g. proximal sesamoid bone (PSB) fracture, third metacarpal/metatarsal (MC3/MT3) fracture, mixed fracture (MC3/MT3+PSB+/–first phalanx), carpal fracture, or other fracture). Non-injured, pre-race or post-race samples were excluded from the data analysis if the horse failed to race again within three months due to concerns that they may have experienced a non-fatal, but significant injury, during the race, which would confound the data.

Exercise-Induced Changes

A total of 26 horses from the sample population were sampled during both pre-race $TCO_2$ testing and again during post-race testing ("paired samples"—approximately 45 minutes post-race) to evaluate any potential exercise-induced changes in mRNA expression during the timeframes utilized for sample collection noted above.

Sample Processing

Following collection, samples were frozen and stored by the participating jurisdictions until shipment to the University of Kentucky's Maxwell H. Gluck Equine Research Center for analysis. RNA was isolated and qPCR performed in accordance with that previously described in the literature.[57, 58] Relative quantities (RQs) of mRNA expression were calculated using a previously described method (Livak et al. (2000)[59] with a population of sedentary horses used as the baseline calibrator and β-glucuronidase (β-Gus) as the endogenous control gene for all samples. Samples were assayed for the following genes using commercially available, exon-spanning primers and probes (ThermoFisher Scientific, Inc., Waltham, Mass.): β-GUS (Ec03470630_m1), ALOX5AP (Ec03470747_m1), CCL8 (Ec03469486_s1), CD14 (Ec04260516_gH), IGF-1 (Ec03468689_m1), IL-1β (Ec04260298_s1), IL1RN (Ec03468814_m1), IL-6 (Ec03468678_m1), IL-8 (Ec03468860_m1), IL-10 (Ec03468647_m1), IL-17A (Ec03470096_m1), MMP1 (Ec03468020_m1), MMP2 (Ec03469995_m1), MMP9 (Ec03469193_m1), PTGS2 (Ec03467558_m1), SAA1 (Ec04321145_s1), TGFβ (Ec03468030_m1), TLR-4 (Ec03468994_m1), TNF-α (Ec03467871_m1), TNFSF13B (Ec04320166_m1), and VEGFA (Ec03467879_m1). The nucleotide sequences corresponding to ALOX5AP (SEQ ID NO: 1), IGF-1 (SEQ ID NO: 3), IL-6 (SEQ ID NO: 5), MMP2 (SEQ ID NO: 7), IL1RN (SEQ ID NO: 9), MMP9 (SEQ ID NO: 11), and VEGFA (SEQ ID NO: 13) as well as the amino acid sequence (SEQ ID NOS: 2, 4, 6, 8, 10, 12, and 14, respectively) to which mRNA corresponding to such sequences encode are provided in the Sequence Listing accompanying the present disclosure.

Data Analysis

Statistical analyses were performed using SigmaPlot® 14 (Systat Software, Inc., San Jose, CA) and RQ data was logarithmically transformed to achieve normality, when possible. One-way analysis of variance (ANOVA) or one-way ANOVA on ranks were used to examine differences between injured, pre-race, and post-race horses. These tests were also used to examine differences between types of injuries and non-injured horses (pre-race and post-race horses combined). Due to the low number of similar fracture types, those horses with injuries in the "other" category (or for which necropsy records were not available) were included in data analysis involving an aggregate of all injuries, but were excluded from analysis of specific fracture types. A two-way ANOVA was used to assess differences between injured, pre-race, and post-race horses due to age. Student's t-test was utilized to evaluate exercise-induced changes in mRNA expression in paired pre/post-race samples from the same horses. Receiver operating characteristic curves were obtained and data used to calculate specificity and sensitivity. Results for all tests were considered significant at $p<0.05$.

Results

Of the 100 injured horses, approximately 50% were in claiming races, with the remainder of injured horses distributed across other race types. Uniaxial and biaxial proximal sesamoid fractures were the most common injury noted in this study, followed by mixed (MC3/MT3+PSB+/−first phalanx) fractures. Tables 2-6 provide additional information regarding the number of horses in various population groups.

TABLE 2

Sex of Horses

| Sex | Total Number of Samples |
|---|---|
| Female | 257 |
| Male | 105 |
| Gelding | 283 |

TABLE 3

Horses Injured vs. Non-Injured

| Type of Sample | Total Number of Samples |
|---|---|
| Injured | 100 |
| Pre-Race | 336 |
| Post-Race | 209 |

TABLE 4

Races Entered and Number of Horses Injured

| Type of Race | Total Number of Horses | Number of Injured Horses |
|---|---|---|
| Claiming (incl. Maiden) | 298 | 50 |
| Starter Optional Claim | 8 | 1 |
| Starter Allowance | 19 | 4 |
| Maiden Special Weight | 67 | 18 |
| Allowance Optional Claiming | 70 | 12 |
| Allowance | 29 | 5 |
| Non-Graded Stakes | 39 | 3 |
| Graded Stakes | 115 | 7 |

TABLE 5

Injuries Sustained by Injured Horse Population

| Type of Injury | Total Number of Horses |
|---|---|
| PSB Fracture | 38 |
| MC3/MT3 Fracture | 13 |
| Mixed Fracture | 25 |
| Carpal Fracture | 9 |
| Other Fracture | 6 |
| Unknown | 9 |

TABLE 6

Age of Horses

| Age (Years) at Time of Sampling | Total Number of Horses | Number of Injured Horses |
|---|---|---|
| 2 | 44 | 12 |
| 3 | 211 | 34 |
| 4 | 208 | 32 |
| 5 | 87 | 10 |
| 6 | 44 | 6 |
| 7 | 33 | 5 |
| 8 | 10 | 0 |
| 9 | 6 | 1 |
| 10 | 2 | 0 |

Paired pre-race and post-race samples from the same horses were used to evaluate effects of exercise on mRNA expression at the time of post-race sampling. Table 7 shows those genes where there was a significant change in expression between pre-race and post-race mRNA expression, along with whether the expression increased or decreased and the associated p-value. Based on these results, those markers that demonstrated an exercise effect, i.e., those provided in Table 7, were excluded from further analyses (n=12). In total, eight remaining genes were analyzed for differences between injured and non-injured horses. Of those eight genes, only four demonstrated significant differences.

TABLE 7

Genes, direction of expression change, and p-values for those excluded from further data analysis based on changes in mRNA expression between pre-race and post-race paired samples.

| Gene | Post-Race Sample Expression | P-value |
| --- | --- | --- |
| CCL8 | Decreased | 0.029 |
| CD14 | Increased | 0.001 |
| IL-10 | Increased | 0.001 |
| IL-1β | Decreased | 0.008 |
| IL1RN | Decreased | 0.009 |
| IL-8 | Increased | 0.003 |
| MMP9 | Decreased | 0.031 |
| PTGS2 | Decreased | 0.001 |
| TGFb | Increased | 0.029 |
| TLR4 | Increased | 0.001 |
| TNFSF13B | Increased | 0.003 |
| VEGFA | Decreased | 0.029 |

Figure 2:
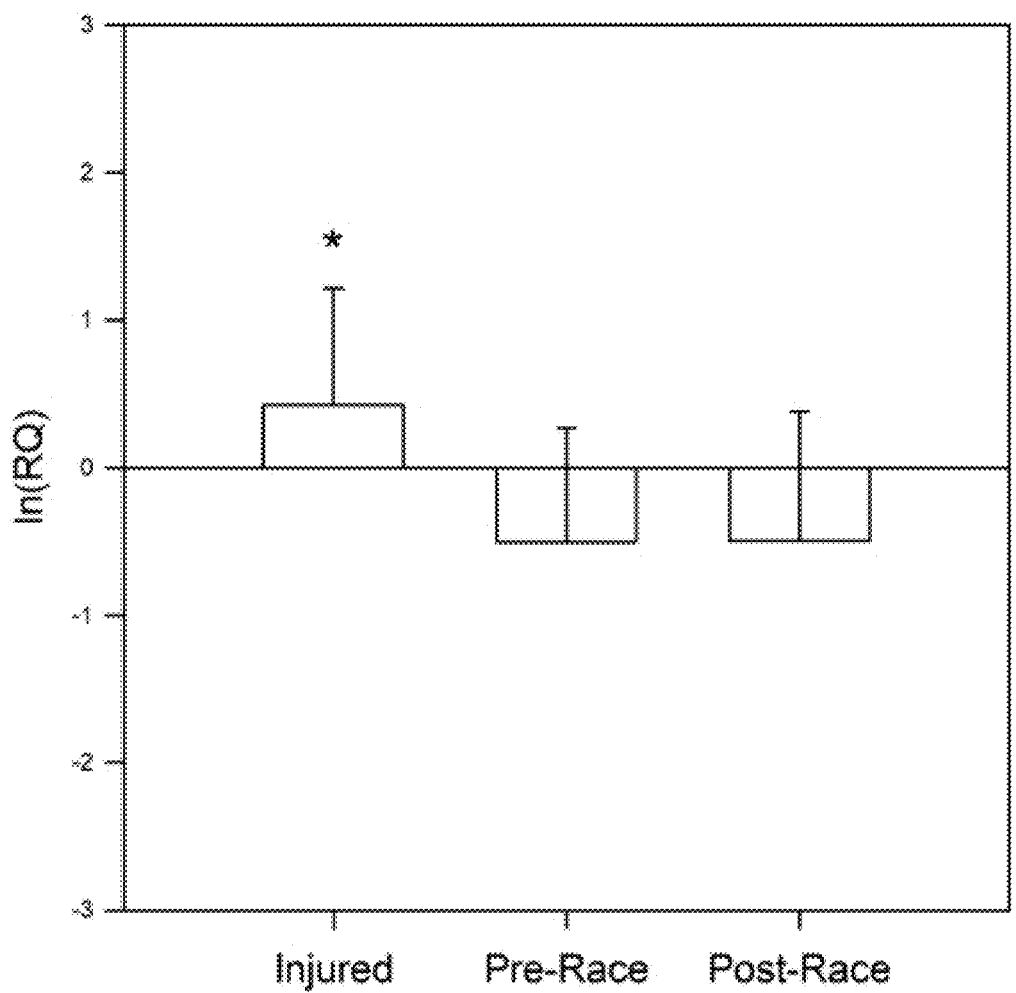
FIG. 2 shows a comparison of mRNA expression of IGF-1 expression (ln(Relative Quantity)) between catastrophically injured horses and non-injured horses sampled either pre-race or post-race.
Figure 3:
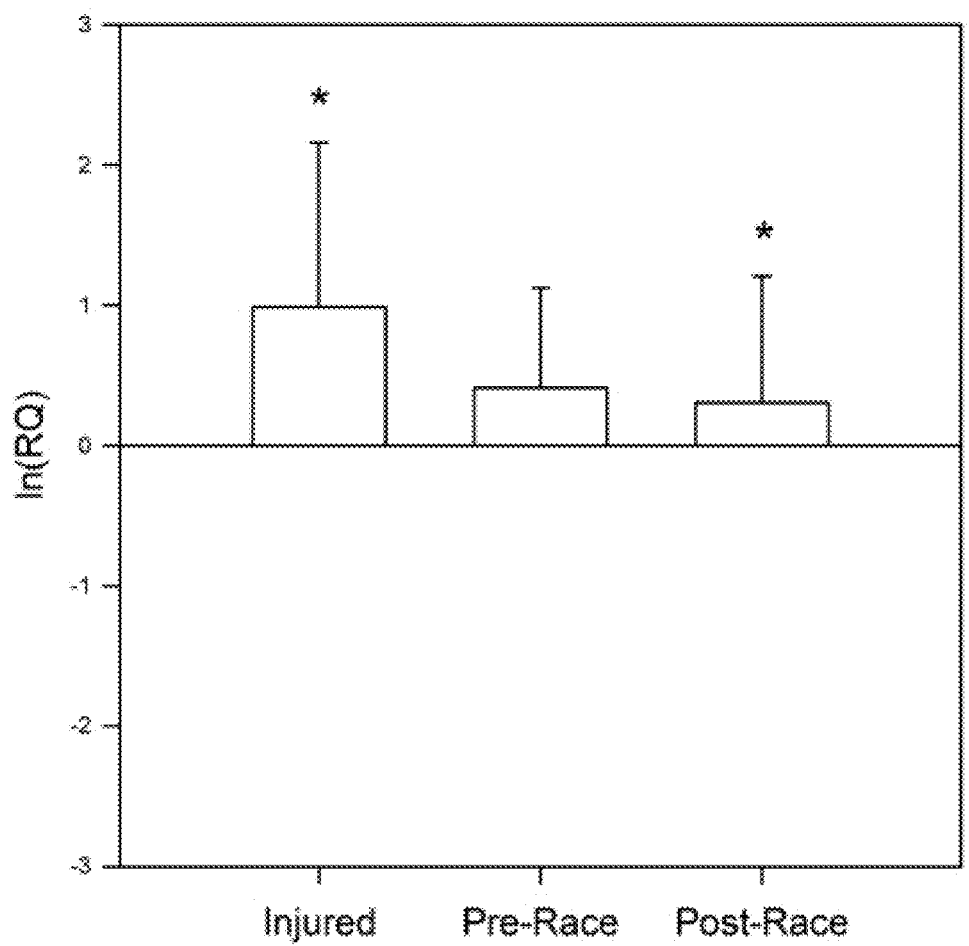
FIG. 3 shows a comparison of mRNA expression of IL-6 expression (ln(Relative Quantity)) between catastrophically injured horses and non-injured horses sampled either pre-race or post-race.
Figure 4:
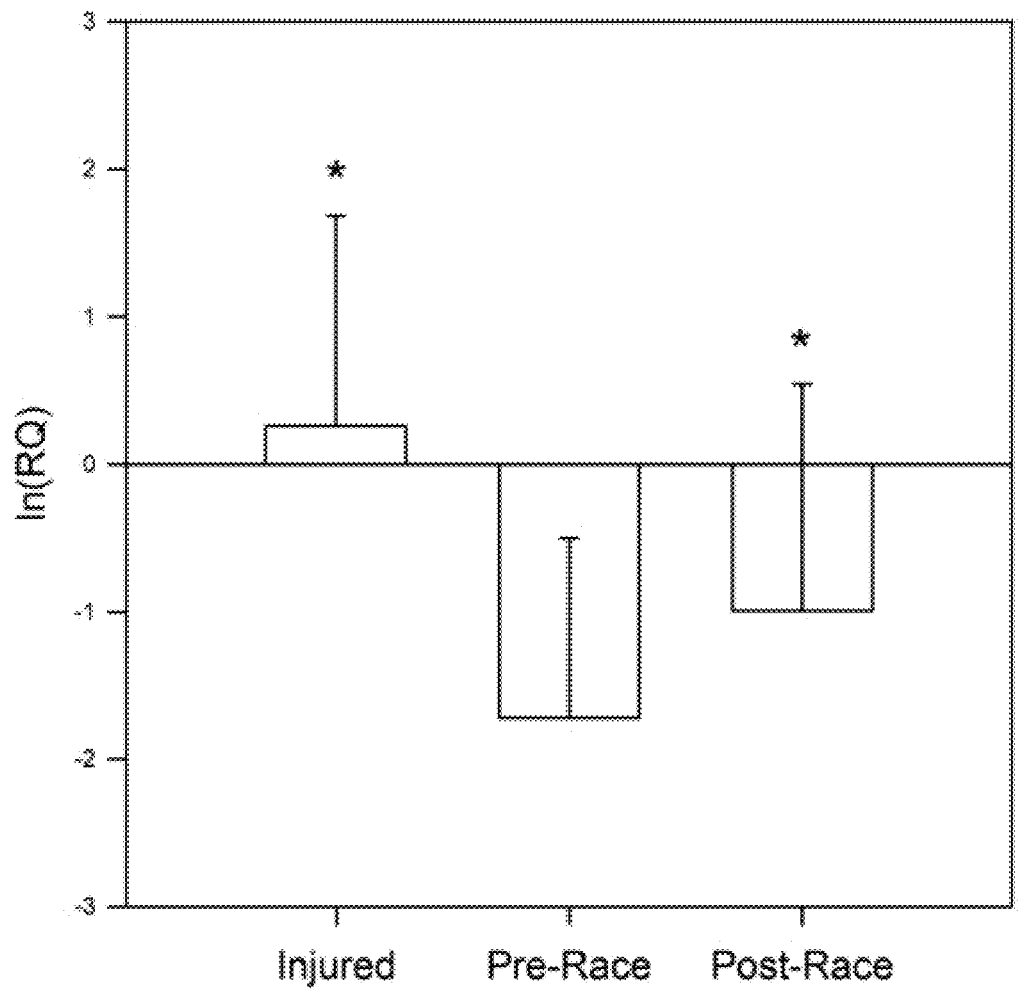
FIG. 4 shows a comparison of mRNA expression of MMP2 (ln(Relative Quantity)) expression between catastrophically injured horses and non-injured horses sampled either pre-race or post-race.

ALOX5AP expression was significantly lower in injured horses when compared to the non-injured control groups (FIG. 1). Conversely, IGF-1, IL-6, and MMP2 were significantly increased in injured horses (FIGS. 2, 3, and 4, respectively). There were no significant differences between control groups with respect to ALOX5AP and IGF-1 expression, whereas, when compared to pre-race controls, post-race controls had significantly lower expression of IL-6 (FIG. 3) and significantly higher expression of MMP2 (FIG. 4).

Figure 5:
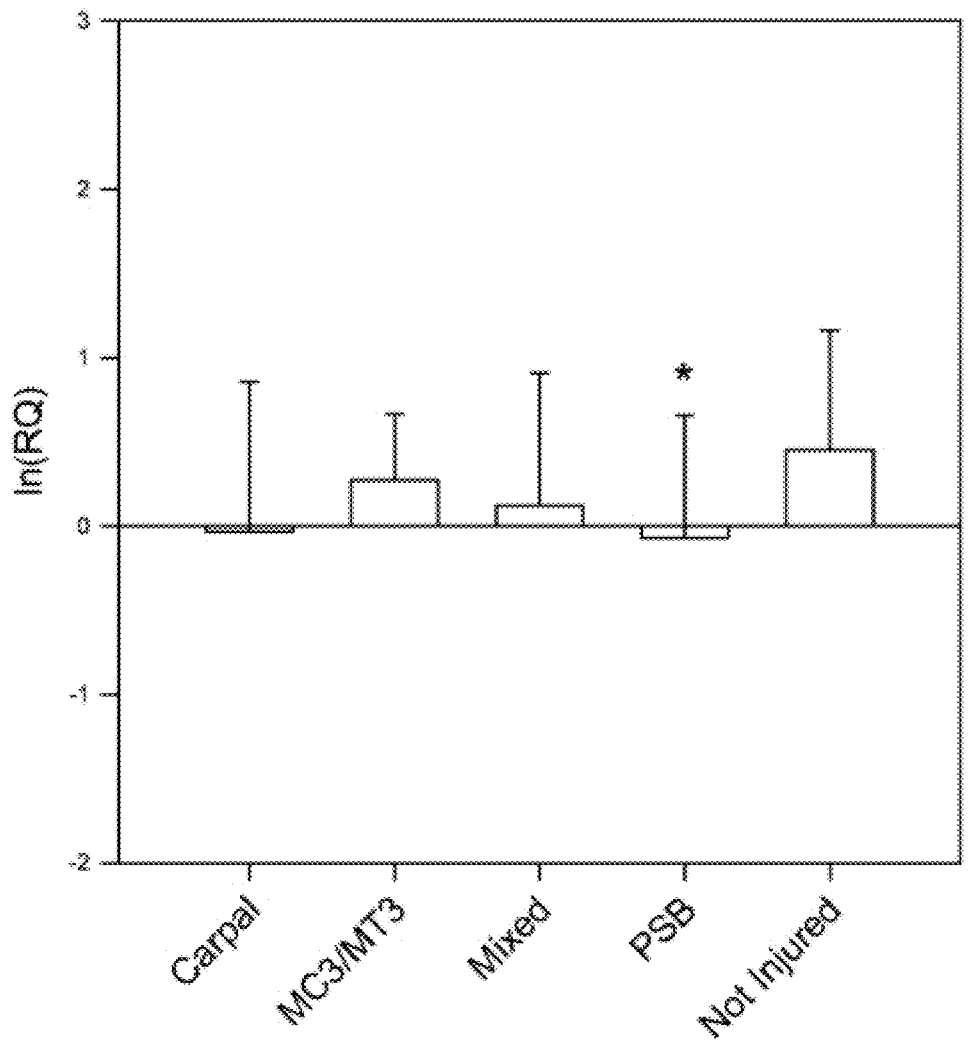
FIG. 5 shows a comparison of mRNA expression of ALOX5AP expression (ln(Relative Quantity)) between catastrophic injury types (carpal fracture, third metacarpal/third metatarsal (MC3/MT3)) fracture, mixed fractures, or proximal sesamoid bone (PSB) fracture) and non-injured horses.
Figure 6:
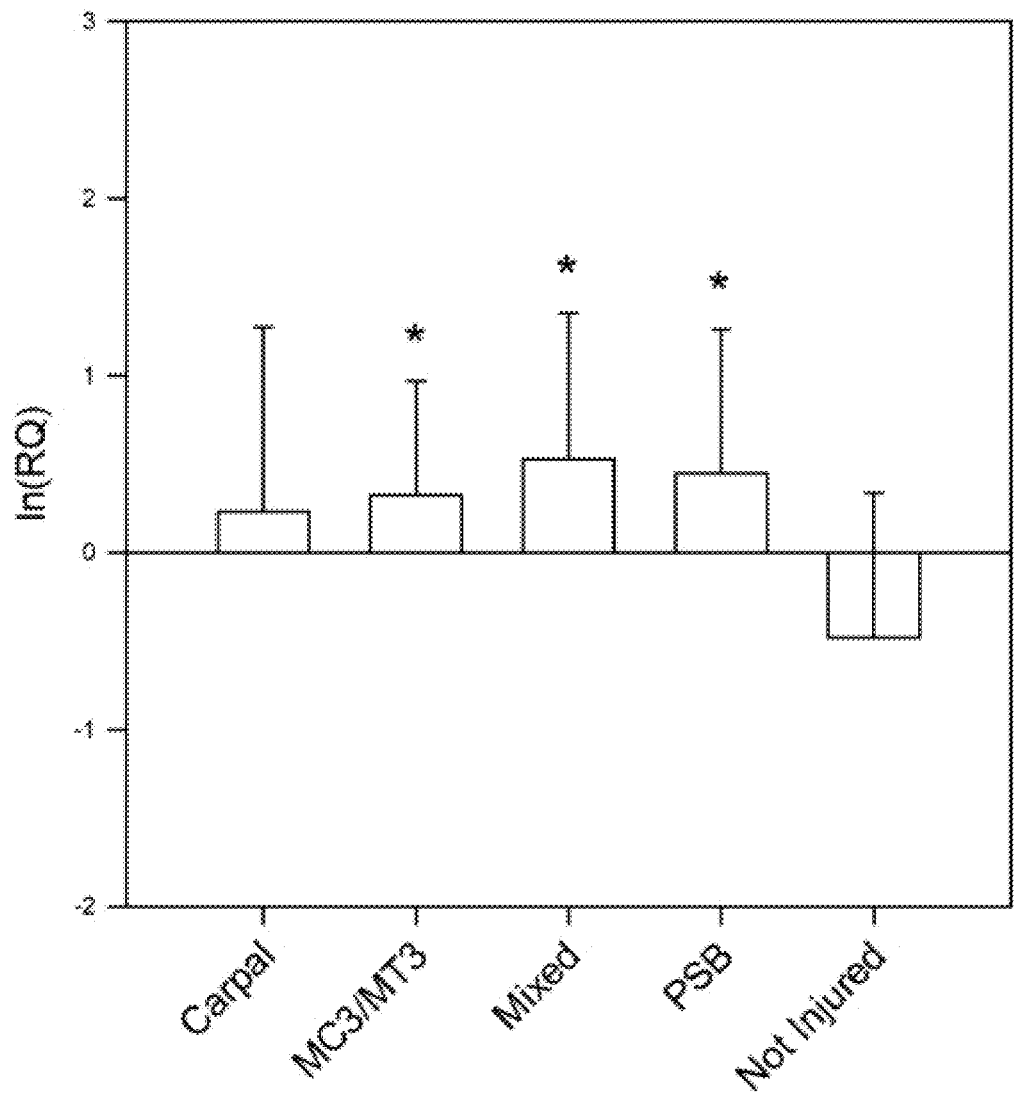
FIG. 6 shows a comparison of mRNA expression of IGF-1 expression (ln(Relative Quantity)) between catastrophic injury types (carpal fracture, third metacarpal/third metatarsal (MC3/MT3)) fracture, mixed fractures, or proximal sesamoid bone (PSB) fracture) and non-injured horses.
Figure 7:
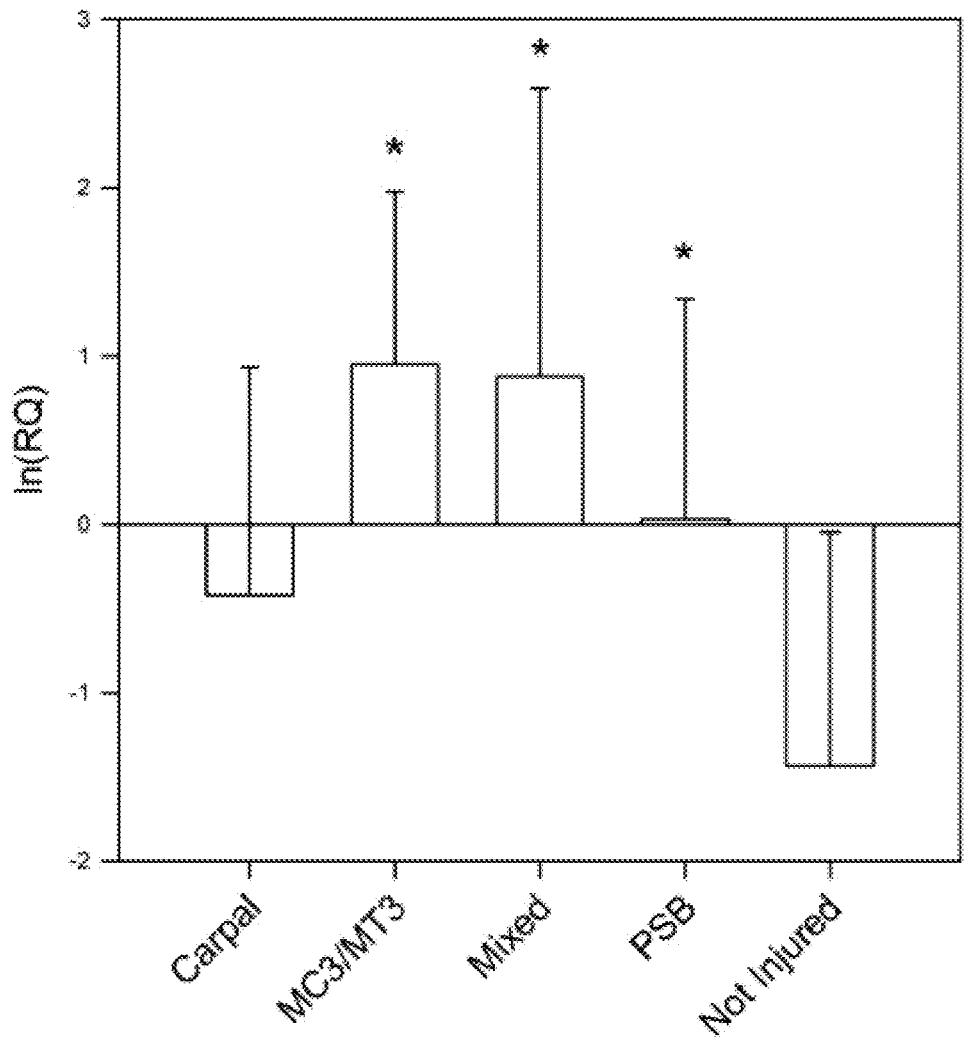
FIG. 7 shows a comparison of mRNA expression of MMP2 expression (ln(Relative Quantity)) between catastrophic injury types (carpal fracture, third metacarpal/third metatarsal (MC3/MT3)) fracture, mixed fractures, or proximal sesamoid bone (PSB) fracture) and non-injured horses.
Figure 8:
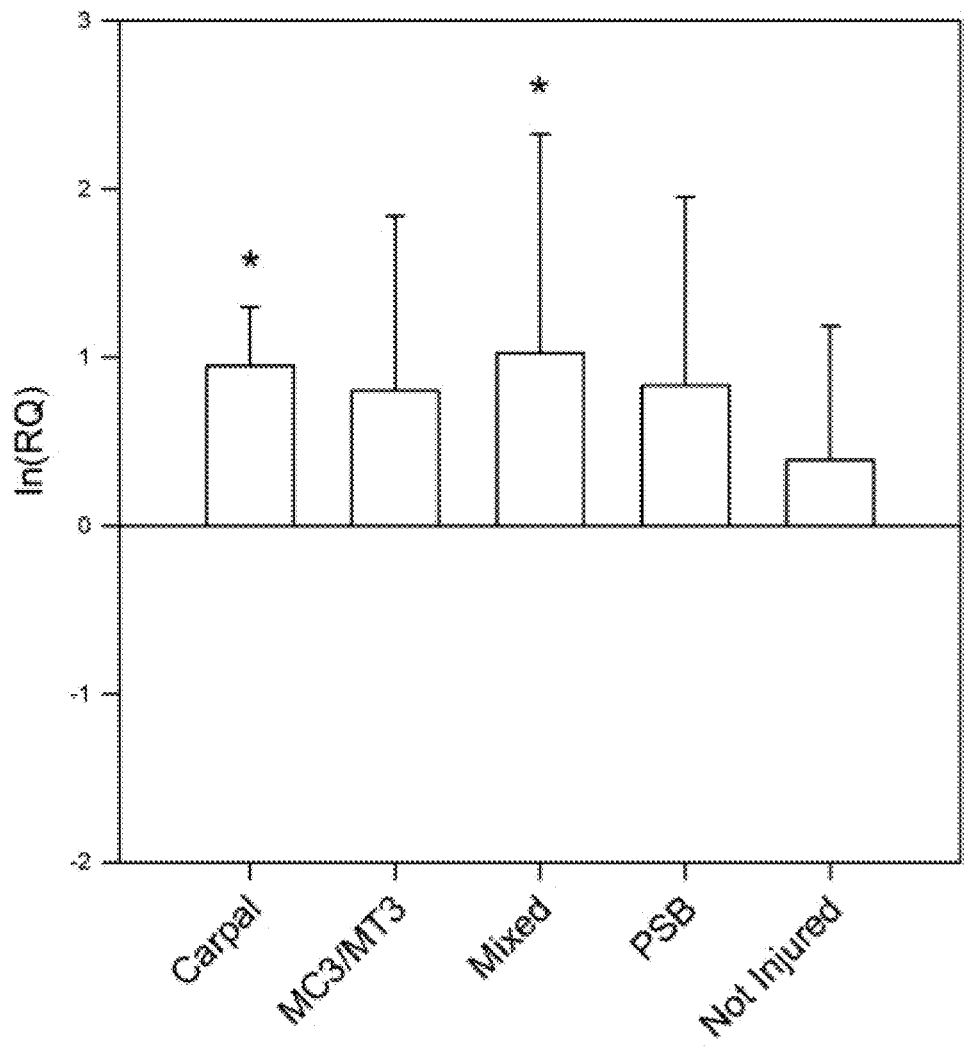
FIG. 8 shows a comparison of mRNA expression of IL-6 expression (ln(Relative Quantity)) between catastrophic injury types (carpal fracture, third metacarpal/third metatarsal (MC3/MT3)) fracture, mixed fractures, or proximal sesamoid bone (PSB) fracture) and non-injured horses.

When comparing individual injury types (PSB fractures, MC3/MT3 fractures, carpal fractures, and mixed fractures) to all of the control horses, PSB fractures had significantly decreased expression of ALOX5AP compared to controls (FIG. 5). PSB, MC3/MT3, and mixed fractures all had significantly increased expression of IGF-1 and MMP2 compared to controls (FIGS. 6 and 7, respectively) while carpal and mixed fractures had significantly increased IL-6 expression (FIG. 8).

Figure 9:
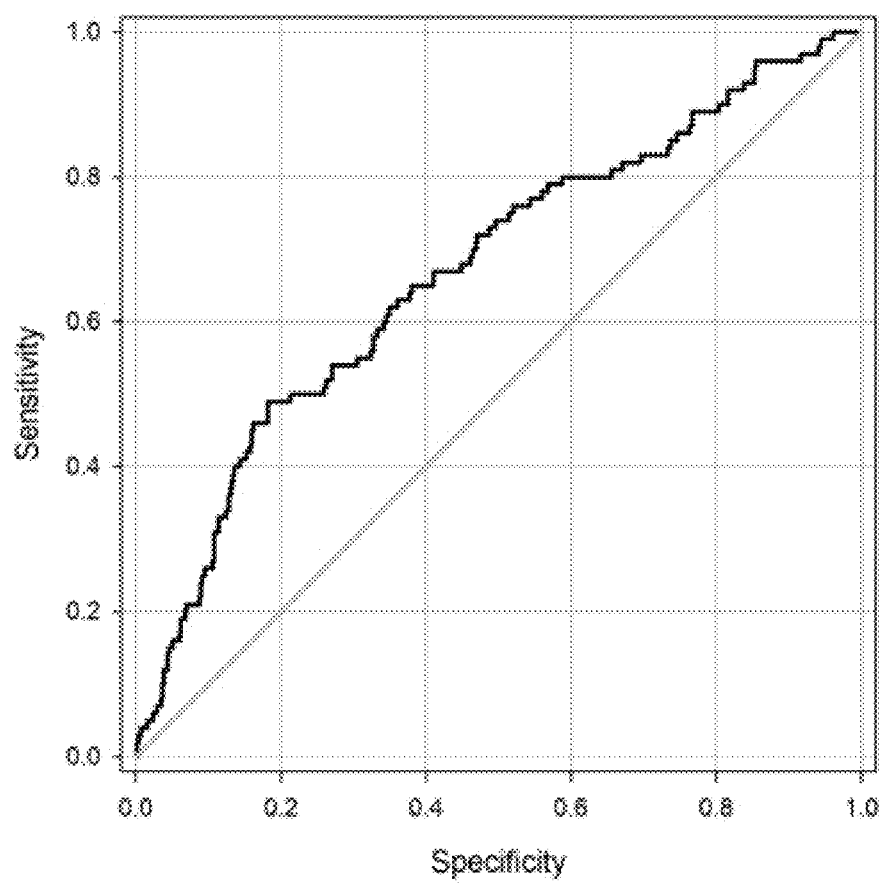
FIG. 9 shows a receiver operating characteristic curve for ALOX5AP (area under the curve=0.670).
Figure 10:
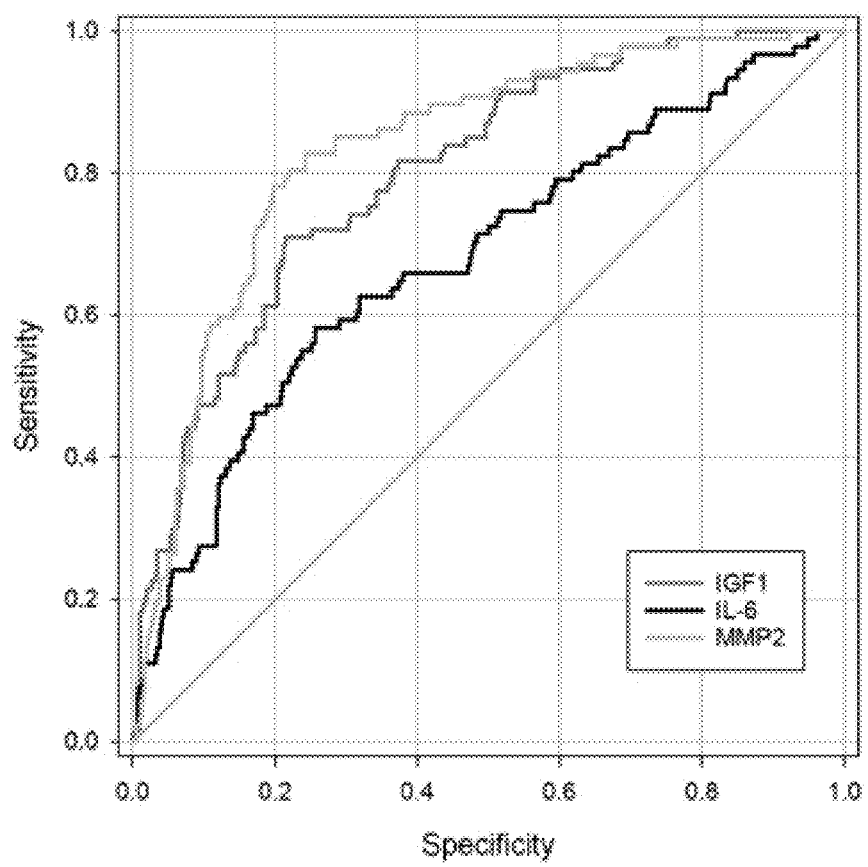
FIG. 10 shows a receiver operating characteristic curves for IGF-1 (area under the curve=0.800), IL-6 (area under the curve=0.679), and MMP2 (area under the curve=0.834).

Receiver operating characteristic curve analysis was used to analyze data for ALOX5AP (FIG. 9), as well as that for IGF-1, IL-6, and MMP2 (FIG. 10), where all injured horses were compared against all non-injured control horses. Based on ROC analysis, IGF-1 (Area=0.800, 95% CI: 0.7532-0.8469) and MMP2 (Area=0.8343, 95% CI: 0.7891-0.8794) had the highest area under the curve values, followed by IL-6 (Area=0.6795, 95% CI: 0.6166-0.7424) and ALOX5AP (Area=0.6700, 95% CI: 0.6102-0.7299). Using this analysis, sensitivities and specificities of approximately 63% (ALOX5AP and IL-6), 72% (IGF-1), and 78% (MMP2) were calculated.

Discussion

As noted above, 100 catastrophically injured and 545 non-injured control horses were enrolled in this prospective study, and the samples were obtained from five different racing jurisdictions across the United States. This yielded a wide variety of catastrophic injury types representing the most common CI's observed in Thoroughbred racing. Not surprisingly, the largest number of CI's in this study involved horses in claiming races, as an increased catastrophic injury risk for claiming horses has been reported previously.[64-66] Here, CI's in claiming races comprised 50% of the total number of CI's that were sampled. Therefore, a large number of non-injured control samples were also collected from claiming races for subsequent analyses.

Older horses have previously been associated with an increased risk for catastrophic injuries.[2, 4, 65, 66] The largest number of CI's in this study were seen in those horses that were 3-4 years old at the time of their injury (66% of all injuries), while horses five years or older only represented 22% of the injuries sampled in this project. This is potentially due to an overrepresentation of younger horses in the entire racing population, although no significant differences were noted between the four genes of interest due to age (data not shown).

Fractures of the proximal sesamoid bones (PSB) are a relatively common catastrophic injury in racehorses,[3, 62-64] as evidenced by the large number of uniaxial and biaxial PSB fractures in this study. Anthenill, et al. has previously described histologic changes in fractured PSBs, as well as PSBs in the contralateral limb.[73] While they noted the ability of these bones to remodel and repair, it was suggested that the remodeling may be excessive and predispose horses to PSB fractures. Although details contained in necropsy reports for this study varied based on the jurisdiction, subjectively, one noted a substantial number of PSB fractures with signs of pre-existing damage associated with the fulminant fracture. The prevention of PSB fractures remain a high-priority as they are difficult to repair and often lead to euthanasia of the horse.

While the collection of only pre-race/pre-injury samples from all horses in the participating jurisdictions would have been preferable, the low incidence of catastrophic injuries during North American racing[17] and the significant logistical challenges of collecting enough pre-race samples to ensure a sufficient number for data analysis (approximately 50,000) necessitated the collection of samples immediately after an injury had occurred (within 30 minutes of the injury). Further, this design was predicated on an understanding that the transcription process, in which DNA is transcribed into mRNA, is both complicated and well-regulated, and thereby taking time to result in significant accumulation of mRNA.[78] This is perhaps best demonstrated by a recent paper, whereupon acute synovitis was induced in horses through an intra-articular lipopolysaccharide injection followed by monitoring of the inflammatory mRNA response over time.[57] In this model, changes in mRNA expression did not reach significant levels until four to six (4-6) hours post-injection, although significant lameness was present by four hours post-injection. While synovitis and fractures experience different pathologies, they are both still ultimately localized sources of significant inflammation and, as such, the synovitis model provides valuable insight into the time-frame over which one would expect expression changes in circulating leukocytes (the sample medium collected using Tempus™ tubes) in relation to an acute inflammatory insult.

Based on prior work demonstrating that inflammatory mRNA expression does not increase until several hours after strenuous exercise,[51, 53] this study also included the sampling of non-injured horses during regulatory post-race drug testing (45 minutes or less post-race). This was undertaken as a means of providing race-matched, non-injured controls under the notion that there would be no significant post-race effects in mRNA expression. Therefore, paired pre-race and post-race samples were collected from the same horses to verify this assumption. Using these samples, 12 different genes were identified as changing significantly between the two sampling time points and, thus, excluded from further data analysis due to concerns that changes seen in injured horses could be confounded by post-race changes in mRNA expression. It should be noted that of the 12 genes that changed post-race (CCL8, CD14, IL-10, IL-1β, IL1RN, IL-8, MMP9, PTGS2, TGFβ, TLR4, TNFSF13B, and VEGFA), it is believed that only IL-1β had been previously measured in a work, and in such work, it was found to increase post-exercise,[51, 53] rather than decrease as it did here. Following the exclusion of these 12 genes, the remaining eight were analyzed, with four demonstrating potential utility in identifying CI horses.

The expression of ALOX5AP was found to be significantly lower in the injured horse population when compared to non-injured controls. Further, when analyzing specific injury types, PSB fractures were the only injury type with significantly lower ALOX5AP expression, although there was a trend for mixed fractures (p=0.072) and carpal fractures (p=0.087) to also have lower expression. The calculated specificity and sensitivity of ALOX5AP for discerning between injured and non-injured horses was 63%. ALOX5AP encodes the 5-lipoxygenase protein, which is necessary for the creation of pro-inflammatory leukotrienes from arachidonic acid. Interestingly, previous work with ALOX5AP in horses has shown it to increase in response to exercise[58] and following induction of acute, localized inflammation.[57] Therefore, the divergent results with this study, in which increased expression would be anticipated, was unexpected and the reason not readily apparent.

While analysis of the paired pre-race and post-races samples showed there was a trend for IL-6 expression to be decreased post-race (p=0.070), this was more evident in the population of post-race, non-injured controls as they had significantly lower expression compared to the pre-race, non-injured controls. Of particular importance is the fact that IL-6 expression was significantly increased in injured horses compared to non-injured controls, suggesting that, if anything, injured horse expression levels may actually be artificially reduced due to the timing of post-injury samples. Further, IL-6 expression was increased in both carpal fractures and mixed fractures compared to non-injured controls. The calculated specificity and sensitivity of IL-6 for discerning between injured and non-injured horses was 63%.

The expression of both IGF-1 and MMP2 was found to be significantly elevated in injured horses compared to non-injured controls. These two genes were also significantly elevated in PSB, MC3/MT3, and mixed fractures when compared to controls. Interestingly, IGF-1 expression tended to decrease post-race in the paired samples (p=0.082), which matches with data from the acute synovitis model where IGF-1 significantly decreased in the early phase of inflammation, before increasing at approximately 24 hours.[57] This would seem to suggest that IGF-1 mRNA expression may act as a negative acute phase marker, in that its expression decreases during early inflammation. This is particularly important given that IGF-1 expression was increased here in injured horses, suggesting that increases in IGF-1 are more indicative of chronic inflammation, as one might expect to see pre-injury in horses at risk for CI's. Furthermore, it is known that IGF-1 plays a substantial part in bone development and repair,[68, 69] including a possible synergistic role in combination with MMP2.[70] By itself, MMP2 is an important component of fracture remodeling, suggesting a possible chronic role in catastrophically injured horses, especially when CI's are associated with areas of pre-existing damage.[18-25] Taken together, this may explain why both IGF-1 and MMP2 appear to be suitable candidate markers for CI horses based on sensitivity/specificities of 72% (IGF-1) and 78% (MMP2).

In view of the foregoing, ALOX5AP, IL-6, IGF-1, and MMP2, alone or in combination, may thus be suitable candidate biomarkers for identifying horses at risk for a catastrophic injury.

Example 2

Materials and Methods

Horses, Sample Collection, and Inclusion Criteria

Horses eligible for inclusion in this study were those Thoroughbreds entered into any race in a participating United States jurisdiction (n=5) during the study period. In total, 904 biological samples were taken; however, 218 of the samples were excluded from data analysis, as further described below. In this regard, 686 horses were thus included in the data analysis described herein, of which there were 107 CI horses and 579 were non-injured horses. Of the non-injured horses, 374 were pre-race horses and 205 were post-races horses.

Biological samples taken from the horses consisted of 3 mL of peripheral blood collected into a single Tempus™ blood RNA tube (Applied Biosystems, Inc., Foster City, CA) for total RNA isolation from the three groups of horses. Samples from CI horses were collected within 30 minutes post-injury. From the same race, one or more horses held for post-race drug testing were also sampled within 45 minutes of the race's conclusion (post-race controls). Lastly, samples were collected by participating jurisdictions during random pre-race $TCO_2$ testing (pre-race controls). The investigators were blinded to the status (e.g. injured, pre-race, or post-race) and names of sampled horses by the participating jurisdictions until RNA isolation and qPCR was performed.

Following identification of the blinded samples, publicly available records (www.equibase.com, Equibase Company, LLC, Lexington, Ky.) were used to obtain data on each sampled horse. Data collected included: sex, age, race type, and whether the horse raced again within three months of the sampled race. For injured horses, the race narrative was examined to identify any possible confounding factors related to the injury. As such, injured horses were excluded from the data analysis if they were noted to have clipped heels and fallen, been bumped and fallen, fallen over another horse, or experienced sudden death. Necropsy results were obtained for all CI horses and utilized to categorize the type of musculoskeletal injury that was sustained (e.g. proximal sesamoid bone (PSB) fracture, third metacarpal/metatarsal (MC3/MT3) fracture, mixed fetlock fracture (PSB+/−MC3/MT3+/−first phalanx), carpal bone fracture, or other fracture). Non-injured, pre-race or post-race samples were excluded from the data analysis if the horse failed to race again within three months of the sample collection due to concerns that they may have experienced a non-fatal, but significant injury, during the race.

Exercise-Induced Changes

A total of 37 horses were sampled during both pre-race $TCO_2$ testing and again during post-race testing to evaluate any potential exercise-induced changes in mRNA expression during the timeframes utilized for sample collection of the control samples noted above (within 45 minutes of the end of the race).

Sample Processing

Following collection, samples were frozen and stored by the participating jurisdictions until shipment to the (blinded for review) for processing and analysis. RNA was isolated and qPCR performed as previously described in the literature.[57, 58] Relative quantities (RQs) of mRNA expression were calculated using a previously described method[59] with a population of sedentary horses used as the baseline calibrator for all samples and β-glucuronidase (β-Gus) as the endogenous control gene for all samples.[60] Samples were assayed in duplicate for the following genes using commercially available, exon-spanning primers and probes (Thermo Fisher Scientific, Inc., Waltham, Mass.): β-GUS (Ec03470630_m1), ALOX5AP (Ec03470747_m1), BMP-2 (Ec06974239_m1), CD14 (Ec04260516_gH), IGF-1 (Ec03468689_m1), IL-1β (Ec04260298_s1), IL1RN (Ec03468814_m1), IL-6 (Ec03468678_m1), IL-8 (Ec03468860_m1), IL-10 (Ec03468647_m1), MMP1 (Ec03468020_m1), MMP2 (Ec03469995_m1), MMP9 (Ec03469193_m1), Osteoprotegrin (Ec07007303_m1), PTGS2 (Ec03467558_m1), RANKL (Ec06625532_m1), SAA1 (Ec04321145_s1), TGFβ (Ec03468030_m1), TLR-4 (Ec03468994_m1), TNF-α (Ec03467871_m1), TNFSF13B (Ec04320166_m1), and VEGFA (Ec03467879_m1). These genes were selected based on their role of the proteins they encode in inflammation, bone repair/remodeling, tissue repair, and response to injury. The nucleotide sequences corresponding to ALOX5AP (SEQ ID NO: 1), IGF-1 (SEQ ID NO: 3), IL-6 (SEQ ID NO: 5), MMP2 (SEQ ID NO: 7), IL1RN (SEQ ID NO: 9), MMP9 (SEQ ID NO: 11), and VEGFA (SEQ ID NO: 13) as well as the amino acid sequence (SEQ ID NOS: 2, 4, 6, 8, 10, 12, and 14, respectively) to which such sequences encode are provided in the Sequence Listing accompanying the present disclosure.

Data Analysis

Statistical analyses were performed using SigmaPlot® 14 (Systat Software, Inc., San Jose, CA) and R (R Foundation for Statistical Computing, Vienna, Austria). RQ data was logarithmically transformed to achieve normality, when possible, and results for all tests were considered significant at $P<0.05$. Paired t-tests or signed rank tests were used to examine differences between paired pre-race and post-race samples. Following exclusion of genes demonstrated to change significantly in the post-race period, non-paired pre-race and post-race samples were combined into one group of non-injured control horses to allow for dichotomization of the outcome (injured or non-injured). Multiple logistic regression analysis was then used to analyze the data and models were fit for all remaining genes of interest, all covariates of interest (jurisdiction of collection, sex, age, and category of race (claiming, allowance, or stakes race)), both of these groups of variables combined, and a model including only those genes with significant expression differences between injured and non-injured horses. Odds ratios and 95% confidence intervals were calculated for the model with all genes of interest and covariates included. Area under the curve, as calculated using receiver operating characteristic analysis, in addition to sensitivity and specificity at the Youden Index, was also calculated for all models. Lastly, one-way analysis of variance (ANOVA) on ranks (Kruskal-Wallis) was used to analyze differences in expression of significant genes between types of injuries and non-injured horses.

Results

Figure 11:
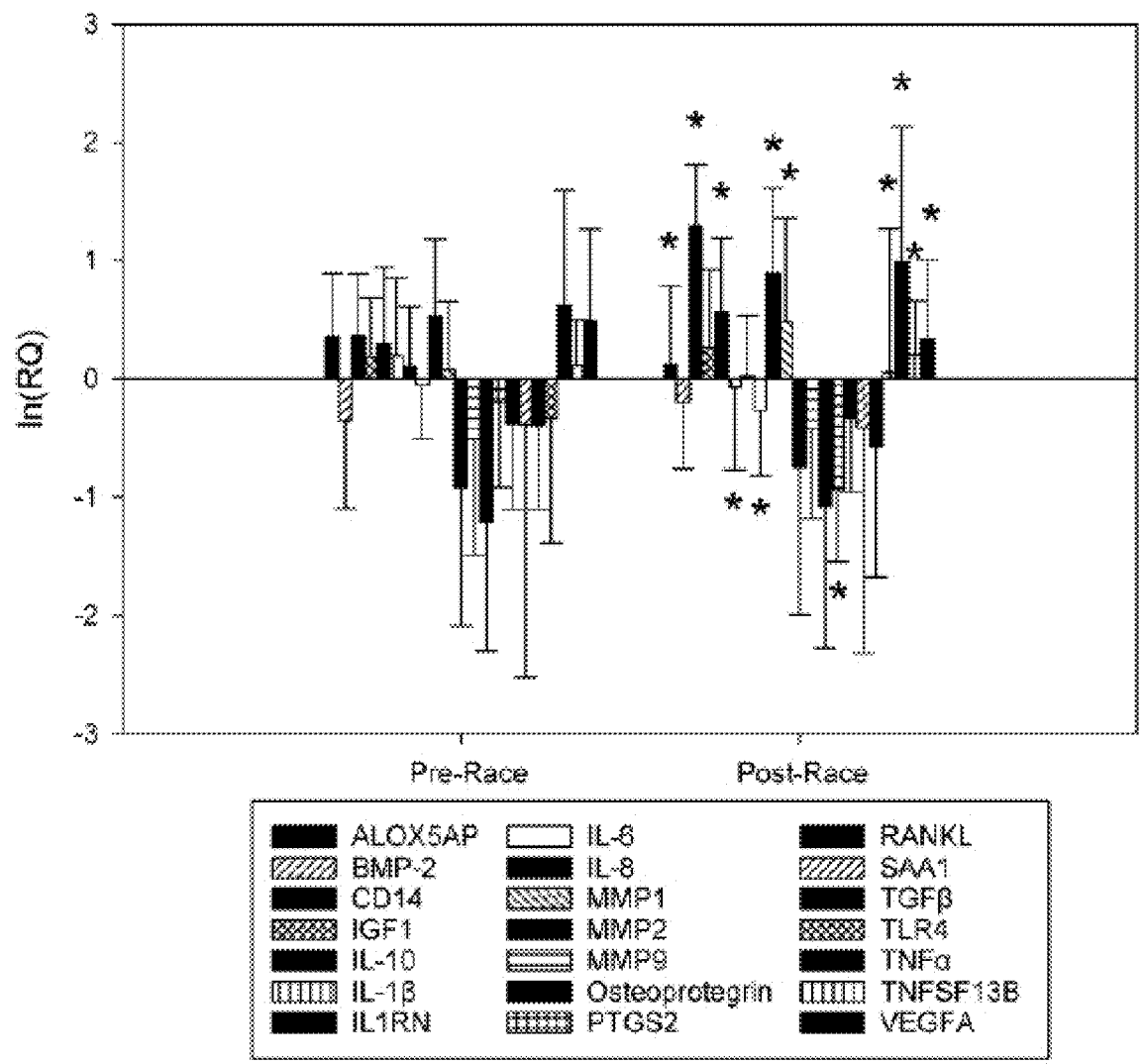
FIG. 11 shows a comparison of mRNA expression (ln (Relative Quantity)) between paired pre-race and post-race samples.

To eliminate those genes whose expression was affected by exercise, a total of 37 horses were sampled both pre-race and post-race within the time-frame utilized in this study for post-race sample collection (approximately 45 minutes). Paired samples were collected at four racetracks from two different participating jurisdictions. Of the 21 measured genes, 12 demonstrated significant differences between the pre-race and post-race time points (FIG. 11 and Table 8) and were excluded from further analysis.

TABLE 8

Genes, direction of expression change in post-race samples compared to pre-race, and P values for those markers excluded from further data analysis based on changes in mRNA expression between paired pre-race and post-race samples (n = 37 horses).

| Gene | Post-Race Sample Expression | P Value |
|---|---|---|
| ALOX5AP | Decreased | 0.008 |
| CD14 | Increased | 0.001 |
| IL-10 | Increased | 0.001 |
| IL-1β | Decreased | 0.007 |
| IL-6 | Decreased | 0.001 |
| IL-8 | Increased | 0.001 |
| MMP1 | Increased | 0.001 |
| PTGS2 | Decreased | 0.001 |
| TLR4 | Increased | 0.001 |
| TNFα | Increased | 0.005 |
| TNFSF13B | Increased | 0.040 |
| VEGFA | Decreased | 0.036 |

Out of 904 total samples collected, 686 were included in the data analysis comparing catastrophically injured and non-injured control horses, representing 107 injured horses, 374 pre-race horses, and 205 post-race horses. Of the 218 excluded samples, 5 were from catastrophically injured horses that either clipped heels or bumped/collided with another horse, 14 were from horses that died acutely from non-orthopedic causes, 26 were from horses with non-fatal injuries, 116 were from pre-race or post-race horses that did not race again within 3 months of the sampling date, 37 were from the post-race sample of horses for which a paired, pre-race sample was also collected, 13 were from horses that were sampled at two different times during the study and a sample was removed, and 7 were excluded for other reasons. Counts and percentages of categorical data with regards to the age at sampling and race types are presented in Tables 9 and 10, while data regarding the racing jurisdictions and sex of sampled horses are presented in Tables 11 and 12, respectively.

TABLE 9

The total number and approximate percentage of samples by age in years at the time of sampling. Percentages are out of the total for the sample type (pre-race, post-race, or injured) or the entire study population.

| Years of Age | Total | Pre-Race | Post-Race | Injured |
|---|---|---|---|---|
| 2 | 45 (6.6%) | 8 (2.1%) | 24 (11.7%) | 13 (12.2%) |
| 3 | 219 (31.9%) | 124 (33.1%) | 61 (29.8%) | 34 (31.8%) |
| 4 | 218 (31.8%) | 124 (33.1%) | 60 (29.3%) | 34 (31.8%) |
| 5 | 94 (13.7%) | 51 (13.6%) | 32 (15.6%) | 11 (10.3%) |
| 6 | 51 (7.4%) | 33 (8.8%) | 11 (5.4%) | 7 (6.5%) |
| 7 | 38 (5.5%) | 20 (5.3%) | 11 (5.4%) | 7 (6.5%) |
| 8 | 12 (1.8%) | 8 (2.1%) | 4 (2.0%) | 0 |
| 9 | 7 (1.0%) | 5 (1.3%) | 1 (0.5%) | 1 (0.9%) |
| 10 | 2 (0.3%) | 1 (0.3%) | 1 (0.5%) | 0 |

TABLE 10

The total number and approximate percentage of samples by type of race. Percentages are out of the total for the sample type (pre-race, post-race, or injured) or the entire study population.

| Race Type | Total | Pre-Race | Post-Race | Injured |
|---|---|---|---|---|
| Graded Stakes | 108 (15.7%) | 86 (23.0%) | 15 (7.3%) | 7 (6.5%) |
| Listed/Black Type Stakes | 39 (5.7%0 | 20 (5.4%) | 15 (7.3%) | 4 (3.7%) |
| Allowance | 33 (4.8%) | 11 (2.9%) | 17 (8.3%) | 5 (4.7%) |
| Starter Allowance | 21 (3.0%) | 11 (2.9%) | 6 (2.9%) | 4 (3.7%) |
| Allowance Optional Claim | 67 (9.8%) | 32 (8.6%) | 23 (11.2%) | 12 (11.2%) |
| Maiden Special Weight | 71 (10.6%) | 23 (6.2%) | 27 (13.2%) | 21 (19.6%) |
| Starter Optional Claim | 5 (0.7%) | 4 (1.1%) | 0 | 1 (0.9%) |
| Claiming | 238 (34.7%) | 133 (35.6%) | 70 (34.2%) | 35 (32.7%) |
| Maiden Claiming | 104 (15.2%) | 54 (14.4%) | 32 (15.6%) | 18 (16.8%) |

TABLE 11

The total number and approximate percentage of samples by racing jurisdiction. Percentages are out of the total for the sample type (pre-race, post-race, or injured) or the entire study population.

| Jurisdiction | Total | Pre-Race | Post-Race | Injured |
|---|---|---|---|---|
| A | 298 (43.44%) | 160 (42.781%) | 95 (46.341%) | 43 (40.187%) |
| B | 301 (43.878%) | 162 (43.316%) | 93 (45.366%) | 46 (42.991%) |
| C | 51 (7.434%) | 35 (9.358%) | 8 (3.902%) | 8 (7.477%) |
| D | 24 (3.499%) | 17 (4.545%) | 3 (1.463%) | 4 (3.738%) |
| E | 12 (1.749%) | 0 | 6 (2.927%) | 6 (5.607%) |
| TOTAL | 686 | 374 | 205 | 107 |

TABLE 12

The total number and approximate percentage of samples by sex. Percentages are out of the total for the sample type (pre-race, post-race, or injured) or the entire study population.

| Sex | Total | Pre-Race | Post-Race | Injured |
|---|---|---|---|---|
| Female | 266 (38.776%) | 148 (39.572%) | 75 (36.585%) | 43 (40.187%) |
| Gelding | 308 (44.898%) | 166 (44.385%) | 94 (45.854%) | 48 (44.86%) |
| Male | 111 (16.181%) | 60 (16.043%) | 35 (17.073%) | 16 (14.953%) |
| Ridgling | 1 (0.146%) | 0 | 1 (0.488%) | 0 |

Approximately 50% of the catastrophically injured horses were in claiming races (claiming or maiden claiming), with the remainder of injured horses distributed across other race types (Table 10). Uniaxial and biaxial proximal sesamoid bone (PSB) fractures were the most common injury noted in this study, followed by mixed fetlock fractures (PSB+/−MC3/MT3+/−first phalanx) (Table 13). The vast majority of injuries occurred in front limbs, with the front left limb accounting for almost half of all catastrophic injuries (Table 14).

TABLE 13

The total number and approximate percentage of samples by injury type.

| Injury Type | Total |
|---|---|
| Carpal bone fracture | 9 (8.4%) |
| MC3 or MT3 fracture | 15 (14.0%) |

TABLE 13-continued

The total number and approximate percentage of samples by injury type.

| Injury Type | Total |
|---|---|
| Mixed fetlock fracture (PSB +/1 MC3/MT3 +/− first phalanx | 30 (28.0%) |
| PSB fracture | 45 (42.1%) |
| Other fracture | 8 (7.5%) |

MC3, third metacarpal bone.
MT3, third metatarsal bone.
PSB, proximal sesamoid bone.

TABLE 14

The total number and approximate percentage of injured horse samples by the injured limb.

| Injured Limb | Total |
|---|---|
| Right Front | 38 (35.5%) |
| Left Front | 51 (47.7%) |
| Bilateral Front | 2 (1.9%) |
| Right Hind | 9 (8.4%) |
| Left Hind | 6 (5.6%) |
| Bilateral Hind | 1 (0.9%) |

Following analysis of paired samples and the exclusion of 12 race-affected genes, the nine remaining genes (BMP-2, IGF-1, IL1RN, MMP2, MMP9, Osteoprotegrin, RANKL, SAA1, and TGFβ) were analyzed for differences between injured and non-injured horses using multiple logistic regression modeling. Taking into account jurisdiction of collection, sex, age at collection, and category of race (claiming, allowance, or stakes race) as covariates, only three of the nine genes (IGF-1, IL1RN, and MMP2) demonstrated significant differences between catastrophically injured and non-injured control horses (Table 15). The risk for injury was found to be higher in one of the jurisdictions (Jurisdiction E), although the true importance of this is unknown as only 12 samples total were collected from this jurisdiction (Table 11). There were no effects of sex, age, or category of race on the risk for catastrophic injury identified.

TABLE 15

Results from multiple logistic regression modeling. Categories and individual variables are provided, along with odds ratios and 95% confidence intervals for the variable when compared to the category reference, in addition to the associated P-value.

| Category | Variable | OR | 95% CI | P-value |
|---|---|---|---|---|
| Racing Jurisdiction | | | | |
| | Jurisdiction A | Reference | — | — |
| | Jurisdiction B | 1.39 | 0.72-2.74 | 0.3 |
| | Jurisdiction C | 2.25 | 0.71-6.82 | 0.2 |
| | Jurisdiction D | 1.49 | 0.31-6.3 | 0.6 |
| | Jurisdiction E | 7.52 | 1.3-44.92 | 0.02 |
| Sex | | | | |
| | Female | Reference | — | — |
| | Gelding | 0.58 | 0.3-1.16 | 0.1 |
| | Horse | 0.67 | 0.31-1.69 | 0.5 |
| Age | | | | |
| | Age | 0.87 | 0.68-1.12 | 0.3 |
| Race Category | | | | |
| | Allowance | Reference | — | — |
| | Claiming | 0.85 | 0.43-1.68 | 0.6 |
| | Stakes | 0.54 | 0.2-1.37 | 0.2 |
| Gene Expression | | | | |
| | BMP-2 | 0.72 | 0.41-1.24 | 0.2 |
| | IGF1 | 3.2 | 2.06-5.12 | <0.001 |

TABLE 15-continued

Results from multiple logistic regression modeling. Categories and
individual variables are provided, along with odds ratios and 95%
confidence intervals for the variable when compared to the
category reference, in addition to the associated P-value.

| Category | Variable | OR | 95% CI | P-value |
|---|---|---|---|---|
| | IL1RN | 0.14 | 0.06-0.3 | <0.001 |
| | MMP2 | 1.92 | 1.54-2.43 | <0.001 |
| | MMP9 | 1.73 | 0.96-3.27 | 0.08 |
| | Osteoprotegrin | 1.02 | 0.73-1.44 | 0.9 |
| | RANKL | 1.16 | 0.81-1.72 | 0.4 |
| | SAA1 | 1.19 | 1-1.43 | 0.05 |
| | TGFβ | 1.3 | 0.89-2.09 | 0.2 |

OR, odds ratio.
95% CI, 95% confidence interval.

Figure 12:
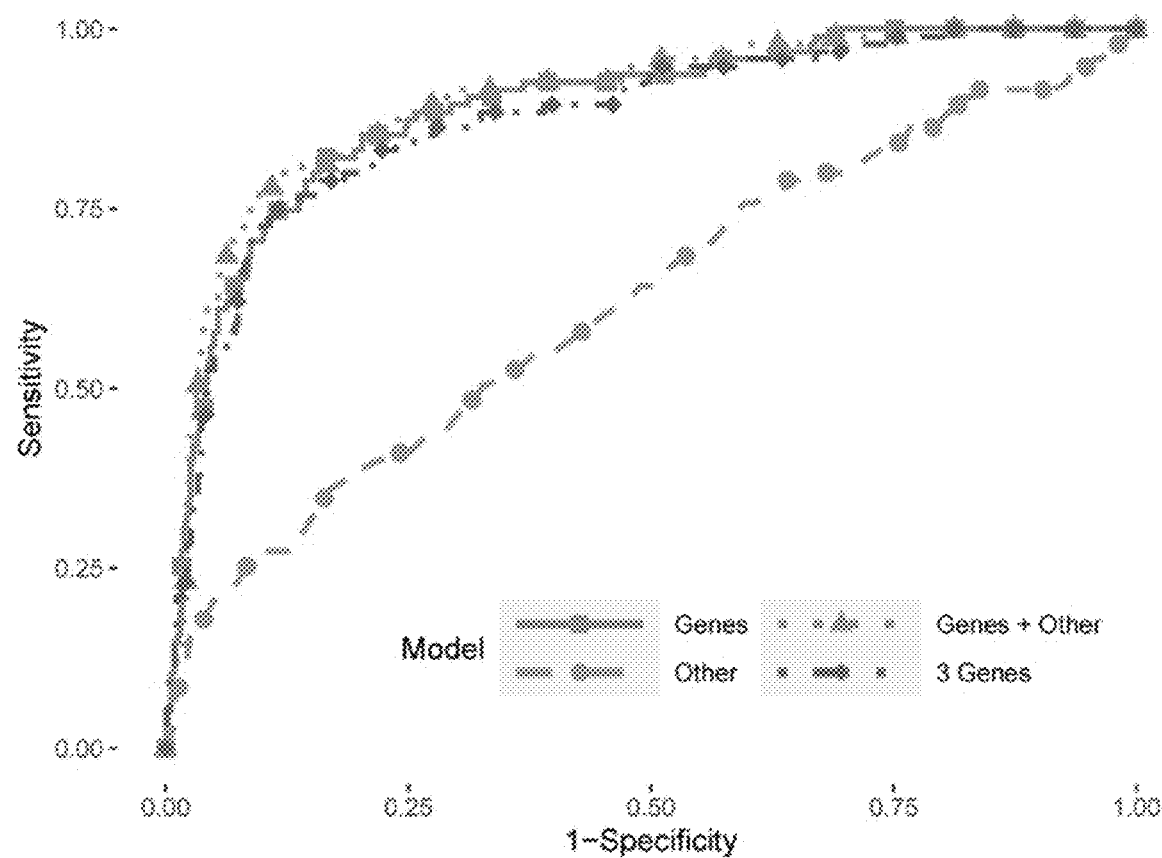
FIG. 12 shows a receiver operating characteristic curve analysis results for all models (nine genes of interest: bone morphogenetic protein 2 (BMP-2); IGF-1; IL1RN; MMP2; matrix metallopeptidase 9 (WP-9); Osteoprotegrin; receptor activator of nuclear factor kappa-B ligand (RANKL); serum amyloid A1 (SAA1); and transforming growth factor beta 1 (TGFβ) (identified as "Genes"), all covariates of interest (identified as "Other"), both of these groups of variables combined (identified as "Genes+Other"), and a model including only the three genes with significant differences (IGF-1, IL1RN, and MPP2 (identified as "3 Genes")).
Figure 14:
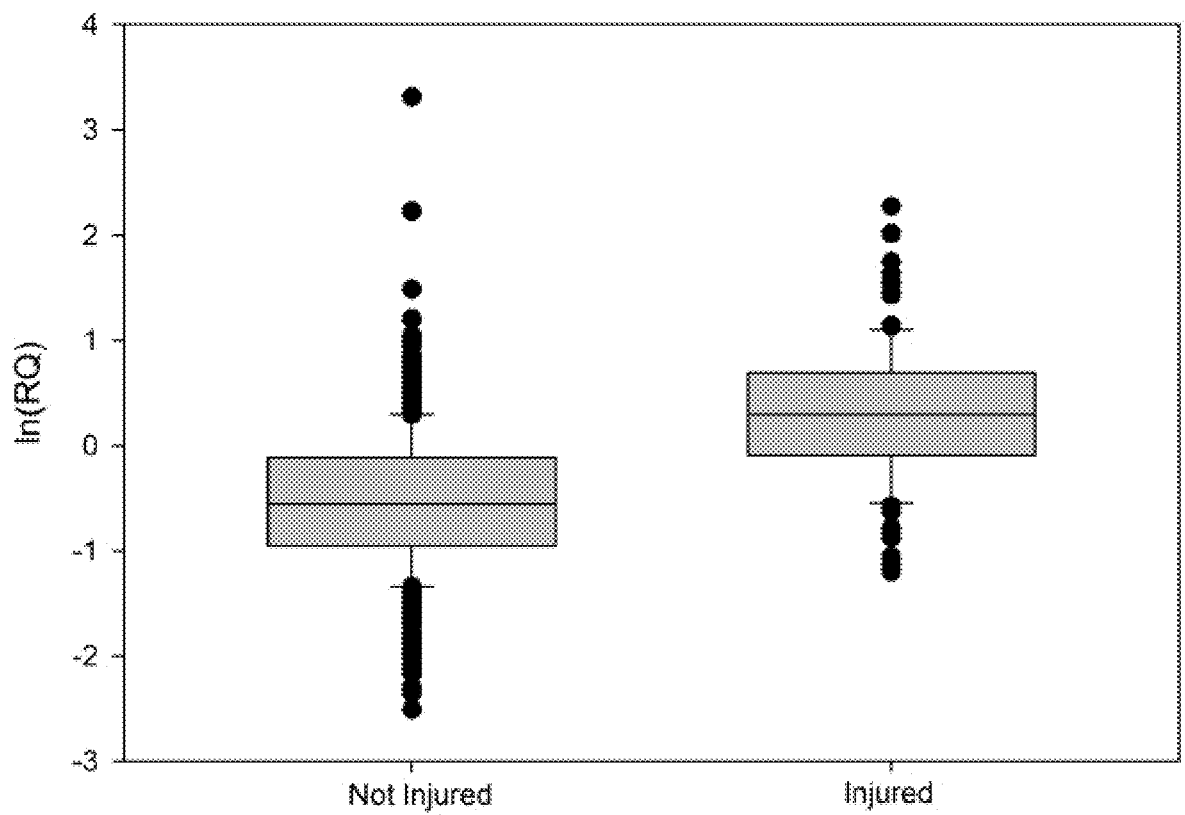
FIG. 14 shows a comparison of mRNA expression of combined IGF-1, IL1RN, and MMP2 expression (ln(Relative Quantity)) between catastrophically injured horses and non-injured horses.

In combination, IGF-1, IL1RN, and MMP2 expression was found to be higher in injured horses when compared to the non-injured horses (FIG. 14). Receiver operating characteristic curve analysis was used to assess data for each model (nine genes of interest (identified as "Genes"), all covariates of interest (identified as "Other"), both of these groups of variables combined (identified as "Genes+Other"), and a model including only the three genes with significant differences (identified as "3 Genes")) (FIG. 12). Area under the curve (AUC), as well as calculated sensitivity and specificity at the Youden Index, is presented for each model in TABLE 16.

TABLE 16

Area under the curve (AUC) from receiver operating characteristic curve
analysis results for all models shown in FIG. 12 (nine genes of interest
(identified as "Genes"), all covariates of interest (identified as "Other"),
both of these groups of variables combined (identified as "Genes +
Other"), and a model including only the three genes with significant
differences (identified as "3 Genes"). Sensitivity and specificity were
calculated at the Youden Index.

| Model Name | AUC | Sensitivity | Specificity |
|---|---|---|---|
| Genes | 0.89 | 82% | 84% |
| Other | 0.62 | 39% | 81% |
| Genes + Other | 0.90 | 80% | 88% |
| 3 Genes | 0.88 | 76% | 88% |

Figure 13A:
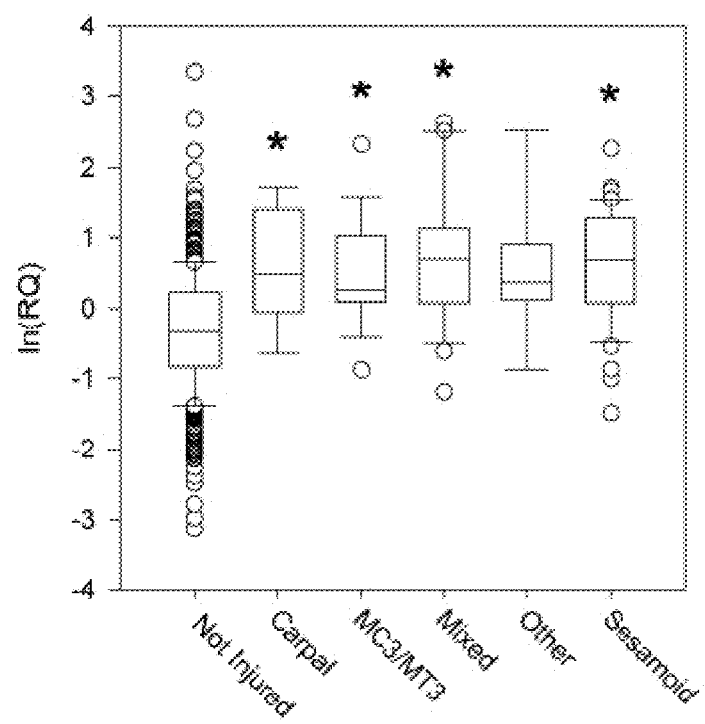
FIG. 13A shows a comparison of mRNA expression of IGF-1 between groups of injured horses (carpal fractures, third metacarpal/third metatarsal bone (MC3/MT3)) fractures, mixed fetlock fractures, other fractures, or sesamoid fractures) compared to non-injured control horses.
Figure 13B:
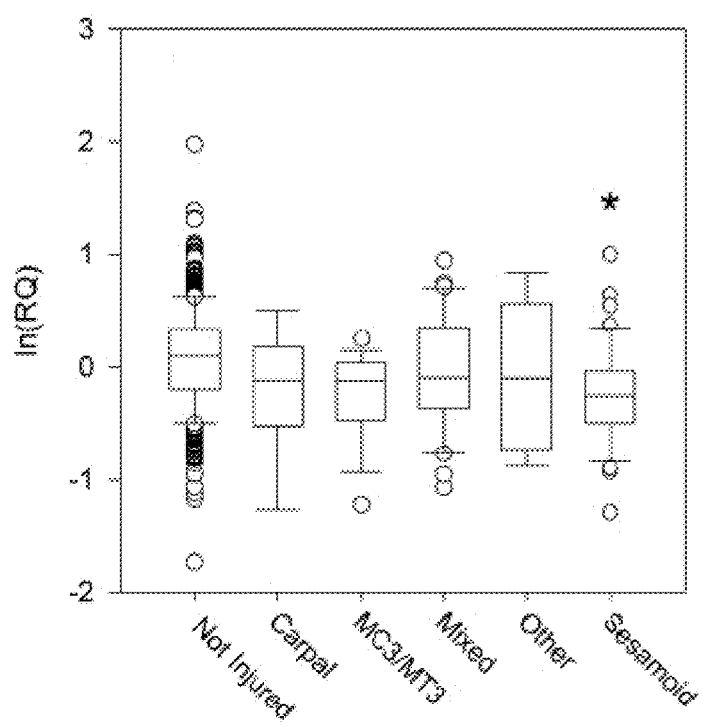
FIG. 13B shows a comparison of mRNA expression of IL1RN between groups of injured horses (carpal fractures, third metacarpal/third metatarsal bone (MC3/MT3)) fractures, mixed fetlock fractures, other fractures, or sesamoid fractures) compared to non-injured control horses.
Figure 13C:
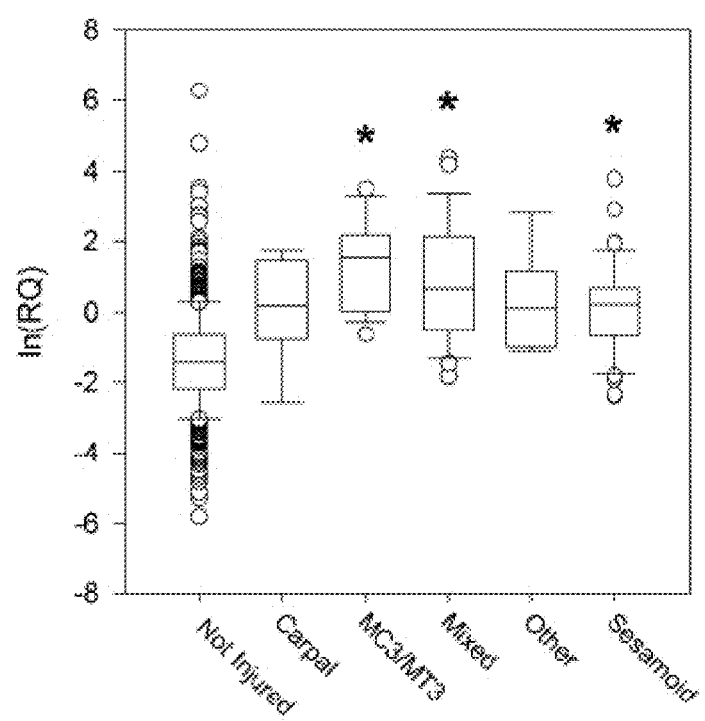
FIG. 13C shows a comparison of mRNA expression of MMP2 between groups of injured horses (carpal fractures, third metacarpal/third metatarsal bone (MC3/MT3)) fractures, mixed fetlock fractures, other fractures, or sesamoid fractures) compared to non-injured control horses.

When comparing individual injury types (carpal fractures, MC3/MT3 fractures, mixed fetlock fractures, other fractures, or sesamoid fractures) to all non-injured control horses, all fracture types except other fractures had significantly elevated expression of IGF-1 (FIG. 13A). Further, only proximal sesamoid bone fractures had significantly lower expression of IL1RN compared to non-injured horses (FIG. 13B), while MC3/MT3 fractures, mixed fetlock fractures, and proximal sesamoid bone fractures all had significantly increased expression of MMP2 (FIG. 13C).

Discussion

While the collection of only pre-race/pre-injury samples from all horses in the participating jurisdictions would have been preferable, the relatively low incidence of catastrophic injuries during North American racing (1.53-1.68 fatalities/1,000 starts during this study),[17] as well as the significant logistical challenges of collecting enough pre-race samples to ensure a sufficient number for data analysis (approximately 70,000 samples), made this impractical. Thus, by collecting samples immediately after an injury (within 30 minutes), the goal of the study was to approximate steady-state mRNA of select genes reflecting the pre-race status of these loci. Further, sampling of non-injured horses at the time of regulatory post-race drug testing (approximately 45 minutes or less post-race) was included as a means of providing race-matched, non-injured controls. While this was predicated on prior work demonstrating inflammatory mRNA expression does not increase until several hours after strenuous exercise,[51,53] those studies did not involve racing. As such, paired pre-race and post-race samples were collected from the same horses at a variety of tracks to validate the lack of mRNA expression changes in the post-race period. Using paired samples, 12 different genes were identified as changing significantly between the two sampling time points and were excluded from further data analyses due to concerns that changes seen in injured horses could be confounded by post-race changes in mRNA expression. It should be noted that of these genes (ALOX5AP, CD14, IL-10, IL-1β, IL-6, IL-8, MMP1, PTGS2, TLR4, TNFα, TNFSF13B, and VEGFA), only IL-1β, TNFα, and IL-6 were measured in the previous work, in which IL-6 did not change post-exercise, IL-1β increased post-exercise rather than decrease as it did in the present example, and TNFα increased post-exercise, but not until several hours after exercise.[51,53] The fact that the samples collected here were post-race, while those reported previously were post-training or post-treadmill exercise, would seem to suggest that the intensity of exercise experienced in racing is more pronounced and more apt to elicit rapid mRNA changes than less strenuous bouts of exercise. Alternatively, the effect of racing on other systemic sources of inflammation, such as the gastrointestinal and respiratory tracts, could also be a contributor to the changes in expression noted here. Once race effects were eliminated, pre-race and post-race control samples were combined during subsequent data analyses.

It is unlikely that the acute orthopedic injury itself contributed to changes in gene expression given the timeframe of the sampling employed here. This is perhaps best demonstrated by a recent paper (Page et al. 2020), whereupon acute synovitis was induced in horses through an intra-articular lipopolysaccharide (LPS) injection followed by monitoring of the inflammatory mRNA response over time.[57] In this model, mRNA expression did not change significantly until 4-6 hours post-injection, although significant lameness was present by 4 hours post-injection. Further, systemic LPS administration has been shown to not result in a significant increase in pro-inflammatory mRNA expression until 2 hours post-injection.[61] While synovitis and fractures may experience different pathologies, they are both still localized sources of significant inflammation and, as such, the LPS-induced acute synovitis model provides valuable insight into the timeframe over which one would expect gene expression changes in circulating leukocytes (the sample medium collected using Tempus tubes) in relation to an acute, localized inflammatory insult.

The samples from 107 CI horses and 579 non-injured control horses gathered across the five jurisdictions provided a wide variety number of catastrophic injury types representing the most common CI's observed in Thoroughbred racing. Among catastrophic injuries in racehorses, fractures involving the proximal sesamoid bones (PSB) are the most common.[3,62-64] Our data is consistent with these reports as 70.1% of CI's in this study involved uniaxial or biaxial PSB fractures. Although there was no significant effect of race category on the occurrence of catastrophic injuries noted here, the largest number of CI's in this study involved horses in claiming races, which is consistent with a reported increased catastrophic injury risk for claiming horses.[64-66] Interestingly, though increased age has previously been associated with an increased risk for catastrophic injuries,[2,4,67] the largest number of CI's in this study was seen in horses aged 2-4 years (75.7% of all injuries), while horses five years or older only represented 24.3% of CI's. This is potentially due to an overrepresentation of younger horses (2-4 years old) in the entire study population (70.3%), although age was not shown to be a potential risk factor for injury in this study.

Following the exclusion of the 12 genes affected by racing, the remaining nine genes were analyzed, with three loci demonstrating potential utility in identifying horses at risk for a CI. The expression of both IGF-1 and MMP2 was found to be significantly elevated in injured horses compared to non-injured controls, with calculated Odds Ratios of 3.2 (95% CI 2.06-5.12) and 1.92 (95% CI 1.54-2.43), respectively. Further, these two genes were also significantly elevated specifically in PSB, MC3/MT3, and mixed fetlock fractures when compared to controls, while IGF-1 was also increased in carpal fractures. Interestingly, it was recently shown that IGF-1 mRNA expression decreases in the early phase of inflammation, before increasing at approximately 24 hours post-acute inflammatory stimulation.[57] This would suggest that IGF-1 mRNA expression may act as a negative acute phase marker and is particularly important given that the study identified IGF-1 expression was increased in catastrophically injured horses. As a result, this may signify that increases in IGF-1 expression are more indicative of chronic inflammation and represent a marker of interest in horses at risk for CI's. It is known that IGF-1 plays a substantial part in bone development and repair,[68,69] including a possible synergistic role with MMP2.[70] By itself, MMP2 is an important component of fracture remodeling,[71] suggesting a possible chronic role in catastrophically injured horses, especially since CI's are often associated with areas of preexisting pathology.[18-25]

The expression of IL1RN, on the other hand, was significantly lower in horses with catastrophic injuries compared to non-injured control horses, an association that was particularly evident in those horses with PSB fractures. Indeed, non-injured horses with increased IL1RN expression had a calculated Odds Ratios of 0.14 (95% CI 0.06-0.3) compared to CI horses. The IL1RN loci is responsible for encoding the protein IL-1 receptor antagonist (IL-1RA), and has previously been shown to correlate well with IL-1β and IL-10 expression in both humans[72] and horses.[57] Since both IL-1β and IL-10 expression were excluded from analysis due to changes between paired pre-race and post-race samples, similar assertions cannot be made here. However, decreased IL1RN expression in CI horses would suggest the presence of a 'pro-inflammatory' state given the potent anti-inflammatory properties of IL-1RA. Furthermore, the finding that only PSB fracture cohorts had significantly lower expression of IL1RN when compared to non-injured controls suggests a possible use for this gene with respect to identifying those horses specifically at risk for a PSB fracture. Anthenill, et al (2010). has previously described histologic changes in fractured PSBs, as well as PSBs in the contralateral limb[73] and, while they noted the ability of these bones to remodel and repair, it was suggested that the remodeling may be excessive and predispose horses to PSB fracture. Although the level of detail contained in necropsy reports for this study varied based on the jurisdiction in which the CI occurred, one jurisdiction noted a substantial number of PSB fractures with signs of pre-existing damage associated with the fracture location. The prevention of PSB fractures remains a high-priority due to their frequency and poor prognosis, which often lead to euthanasia of the injured horse.

In view of the foregoing, IGF-1, MMP2, and IL1RN may thus be suitable candidate biomarkers for identifying horses at risk for a catastrophic injury. As such, receiver operating characteristic analysis was utilized to determine the accuracy and possible utility of the various models to identify horses at risk for a catastrophic injury. Three out of the four models utilized gene expression data from those genes not affected by exercise. From these three models, values for area under the curve (AUC) ranged from 0.88-0.90, while an AUC of 0.62 was obtained using the model comprised solely of covariates. By utilizing the Youden Index, which calculates the cutoff to provide the best sensitivity and specificity for a test, sensitivities from 76-82% and specificities from 84-88% were obtained for the three models that included gene expression data. Of particular note is the model that included only IGF-1, MMP2, and IL1RN expression data, which generated a sensitivity and specificity of 76% and 88%, respectively. While the ability to correctly identify approximately 75% of horses at risk for a CI is a dramatic improvement over the current state of injury risk reduction, sensitivity could be further increased by making adjustments to the cutoff value. This would result in increased sensitivity in identifying horses at risk for catastrophic injuries, though this abundance of caution would come at the cost of specificity. Additional increases in sensitivity and specificity may also arise due to serial sampling of horses on a regular basis, given that expression trends over time could be monitored and abnormal patterns identified. While additional increased sensitivity could be achieved by including covariates in the analysis, the goal is to develop a pre-race risk screening test that could be applied independently of other covariates. As such, based on the results presented here, the three genes (IGF-1, MMP2, and IL1RN) that were identified could prove useful.

Based on communications with the participants, it was expected that more than 90% of the horses would have received a medication within the allowable timeframe for administration. As regulations for pre-race medications change and extend the withdrawal period leading up to a race, it would be expected that any effects of these medications will be lessened and additional changes in mRNA expression could become significant. An added limitation was the omission of detailed risk-factor modeling in combination with the results we reported, however, the goal of this project was to assess mRNA expression rather than risk-factors, which have been examined previously.[2-4,11,66,74-77] Further, while some may question the use of mRNA instead of serum for circulating protein analysis, it was recently demonstrated that inflammatory mRNA expression analysis is more sensitive than protein analysis in horses.[57]

As the racing industry grapples with ways to reduce catastrophic injuries through data-driven regulation and medication changes, there must be a concerted effort to identify at-risk horses beyond the use of epidemiologic modeling. While recent increased interests in advanced imaging is consistent with this goal, the results of the above-described studies have demonstrated that detection of select gene expression through mRNA expression analysis of biological samples acquired from racehorses may provide a more economical, efficient, and non-invasive method of detecting risk for catastrophic injury. To further aid in the identification of racehorses, or other non-human athletic animals, at risk of injury, such method may be utilized in combination with extensive examinations that may include, amongst other things, advanced imaging techniques for those animals identified as being at risk for an injury.

It is appreciated that although the methods disclosed herein may be referred to primarily in the context of non-human athletic animals, and specifically horses, it is appreciated that the various methods disclosed herein may prove useful in detecting gene expression or identifying the risk of injury in other animals as well.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Carrier, T. K., Estberg, L., Stover, S. M., Gardner, I. A., Johnson, B. J., Read, D. H. and Ardans, A. A. (1998) Association between long periods without high-speed workouts and risk of complete humeral or pelvic fracture in thoroughbred racehorses: 54 cases (1991-1994). *J Am Vet Med Assoc* 212, 1582-1587.
2. Cohen, N. D., Berry, S. M., Peloso, J. G., Mundy, G. D. and Howard, I. C. (2000) Association of highspeed exercise with racing injury in thoroughbreds. *J Am Vet Med Assoc* 216, 1273-1278.
3. Cohen, N. D., Peloso, J. G., Mundy, G. D., Fisher, M., Holland, R. E., Little, T. V., Misheff, M. M., Watkins, J. P., Honnas, C. M. and Moyer, W. (1997) Racing-related factors and results of prerace physical inspection and their association with musculoskeletal injuries incurred in thoroughbreds during races. *J Am Vet Med Assoc* 211, 454-463.
4. Georgopoulos, S. P. and Parkin, T. D. (2017) Risk factors for equine fractures in Thoroughbred flat racing in North America. *Prev Vet Med* 139, 99-104.
5. Hill, A. E., Gardner, I. A., Carpenter, T. E. and Stover, S. M. (2004) Effects of injury to the suspensory apparatus, exercise, and horseshoe characteristics on the risk of lateral condylar fracture and suspensory apparatus failure in forelimbs of thoroughbred racehorses. *Am J Vet Res* 65, 1508-1517.
6. Perkins, N. R., Reid, S. W. and Morris, R. S. (2005) Risk factors for musculoskeletal injuries of the lower limbs in Thoroughbred racehorses in New Zealand. *N Z Vet J* 53, 171-183.
7. Vallance, S. A., Entwistle, R. C., Hitchens, P. L., Gardner, I. A. and Stover, S. M. (2013) Case-control study of high-speed exercise history of Thoroughbred and Quarter Horse racehorses that died related to a complete scapular fracture. *Equine Vet J* 45, 284-292.
8. Verheyen, K. L., Price, J. S. and Wood, J. L. (2007) Fracture rate in Thoroughbred racehorses is affected by dam age and parity. *Vet J* 174, 295-301.
9. Anthenill, L. A., Stover, S. M., Gardner, I. A. and Hill, A. E. (2007) Risk factors for proximal sesamoid bone fractures associated with exercise history and horseshoe characteristics in Thoroughbred racehorses. *Am J Vet Res* 68, 760-771.
10. Anderson, T. M., McIlwraith, C. W. and Douay, P. (2004) The role of conformation in musculoskeletal problems in the racing Thoroughbred. *Equine Vet J* 36, 571-575.
11. Parkin, T. D., Clegg, P. D., French, N. P., Proudman, C. J., Riggs, C. M., Singer, E. R., Webbon, P. M. and Morgan, K. L. (2004) Horse-level risk factors for fatal distal limb fracture in racing Thoroughbreds in the UK. *Equine Vet J* 36, 513-519.
12. Kane, A. J., Stover, S. M., Gardner, I. A., Bock, K. B., Case, J. T., Johnson, B. J., Anderson, M. L., Barr, B. C., Daft, B. M., Kinde, H., Larochelle, D., Moore, J., Mysore, J., Stoltz, J., Woods, L., Read, D. H. and Ardans, A. A. (1998) Hoof size, shape, and balance as possible risk factors for catastrophic musculoskeletal injury of Thoroughbred racehorses. *Am J Vet Res* 59, 1545-1552.
13. Estberg, L., Stover, S. M., Gardner, I. A., Drake, C. M., Johnson, B. and Ardans, A. (1996) Highspeed exercise history and catastrophic racing fracture in thoroughbreds. *Am J Vet Res* 57, 15491555.
14. Kane, A. J., Stover, S. M., Gardner, I. A., Case, J. T., Johnson, B. J., Read, D. H. and Ardans, A. A. (1996) Horseshoe characteristics as possible risk factors for fatal musculoskeletal injury of thoroughbred racehorses. *Am J Vet Res* 57, 1147-1152.
15. Hill, A. E., Gardner, I. A., Carpenter, T. E., Lee, C. M., Hitchens, P. L. and Stover, S. M. (2016) Prevalence, location and symmetry of noncatastrophic ligamentous suspensory apparatus lesions in California Thoroughbred racehorses, and association of these lesions with catastrophic injuries. *Equine Vet J* 48, 27-32.
16. Kristoffersen, M., Parkin, T. D. and Singer, E. R. (2010) Catastrophic biaxial proximal sesamoid bone fractures in UK Thoroughbred races (1999-2004): horse characteristics and racing history. *Equine Vet J* 42, 420-424.
17. http://jockeyclub.com/default.asp?section=Advocacy&area=10. (Visited Sep. 18, 2020)
18. Tranquille, C. A., Parkin, T. D. and Murray, R. C. (2012) Magnetic resonance imaging-detected adaptation and pathology in the distal condyles of the third metacarpus, associated with lateral condylar fracture in Thoroughbred racehorses. *Equine Vet J* 44, 699-706.
19. Trope, G. D., Ghasem-Zadeh, A., Anderson, G. A., Mackie, E. J. and Whitton, R. C. (2015) Can high-resolution peripheral quantitative computed tomography imaging of subchondral and cortical bone predict condylar fracture in Thoroughbred racehorses? *Equine Vet J* 47, 428-432.
20. Barr, E. D., Pinchbeck, G. L., Clegg, P. D., Boyde, A. and Riggs, C. M. (2009) Post mortem evaluation of palmar osteochondral disease (traumatic osteochondrosis) of the metacarpo/metatarsophalangeal joint in Thoroughbred racehorses. 41, 366-371.
21. Martig, S., Chen, W., Lee, P. V. and Whitton, R. C. (2014) Bone fatigue and its implications for injuries in racehorses. *Equine Vet J* 46, 408-415.
22. O'Brien, T., Baker, T. A., Brounts, S. H., Sample, S. J., Markel, M. D., Scollay, M. C., Marquis, P. and Muir, P. (2011) Detection of articular pathology of the distal aspect of the third metacarpal bone in thoroughbred racehorses: comparison of radiography, computed tomography and magnetic resonance imaging. *Vet Surg* 40, 942-951.
23. Parkin, T. D., Clegg, P. D., French, N. P., Proudman, C. J., Riggs, C. M., Singer, E. R., Webbon, P. M. and Morgan, K. L. (2006) Catastrophic fracture of the lateral condyle of the third metacarpus/metatarsus in UK racehorses—fracture descriptions and pre-existing pathology. *Vet J* 171, 157-165.
24. Riggs, C. M., Whitehouse, G. H. and Boyde, A. (1999) Pathology of the distal condyles of the third metacarpal and third metatarsal bones of the horse. *Equine Vet J* 31, 140-148.
25. Scollay, M. C. (2017) Autopsy of the racehorse: the regulator's perspective. *Journal of veterinary diagnostic*

26. Hesse, K. L. and Verheyen, K. L. (2010) Associations between physiotherapy findings and subsequent diagnosis of pelvic or hindlimb fracture in racing Thoroughbreds. *Equine Vet J* 42, 234-239.
27. Tranquille, C. A., Murray, R. C. and Parkin, T. D. (2017) Can we use subchondral bone thickness on high-field magnetic resonance images to identify Thoroughbred racehorses at risk of catastrophic lateral condylar fracture? *Equine Vet J* 49, 167-171.
28. Loughridge, A. B., Hess, A. M., Parkin, T. D. and Kawcak, C. E. (2017) Qualitative assessment of bone density at the distal articulating surface of the third metacarpal in Thoroughbred racehorses with and without condylar fracture. *Equine Vet J* 49, 172-177.
29. Peloso, J. G., Vogler, J. B., 3rd, Cohen, N. D., Marquis, P. and Hilt, L. (2015) Association of catastrophic biaxial fracture of the proximal sesamoid bones with bony changes of the metacarpophalangeal joint identified by standing magnetic resonance imaging in cadaveric forelimbs of Thoroughbred racehorses. *J Am Vet Med Assoc* 246, 661-673.
30. Spriet, M., Espinosa-Mur, P., Cissell, D. D., Phillips, K. L., Arino-Estrada, G., Beylin, D., Stepanov, P., Katzman, S. A., Galuppo, L. D., Garcia-Nolen, T., Murphy, B. and Stover, S. M. (2019) 18F-sodium fluoride positron emission tomography of the racing Thoroughbred fetlock: Validation and comparison with other imaging modalities in nine horses. *Equine Veterinary Journal* 51, 375-383.
31. Denoix, J. M. and Coudry, V. (2020) Clinical insights: Imaging of the equine fetlock in Thoroughbred racehorses: Identification of imaging changes to predict catastrophic injury. *Equine Veterinary Journal* 52, 342-343.
32. Blott, S. C., Swinburne, J. E., Sibbons, C., Fox-Clipsham, L. Y., Helwegen, M., Hillyer, L., Parkin, T. D. H., Newton, J. R. and Vaudin, M. (2014) A genome-wide association study demonstrates significant genetic variation for fracture risk in Thoroughbred racehorses. *BMC Genomics* 15, 147.
33. Welsh, C. E., Lewis, T. W., Blott, S. C., Mellor, D. J., Stirk, A. J. and Parkin, T. D. (2014) Estimates of genetic parameters of distal limb fracture and superficial digital flexor tendon injury in UK Thoroughbred racehorses. *Vet J* 200, 253-256.
34. Tozaki, T., Kusano, K., Ishikawa, Y., Kushiro, A., Nomura, M., Kikuchi, M., Kakoi, H., Hirota, K., Miyake, T., Hill, E. W. and Nagata, S. (2020) A candidate-SNP retrospective cohort study for fracture risk in Japanese Thoroughbred racehorses. *Animal Genetics* 51, 43-50.
35. Billinghurst, R. C., Brama, P. A., van Weeren, P. R., Knowlton, M. S. and McIlwraith, C. W. (2003) Significant exercise-related changes in the serum levels of two biomarkers of collagen metabolism in young horses. *Osteoarthritis Cartilage* 11, 760-769.
36. Brama, P. A., van den Boom, R., DeGroott, J Kiers, G. H. and van Weeren, P. R. (2004) Collagenase-1 (MMP-1) activity in equine synovial fluid: influence of age, joint pathology, exercise and repeated arthrocentesis. *Equine Vet J* 36, 34-40.
37. Costa, M. F., Davies, H. M., Anderson, G. A. and Slocombe, R. F. (2011) Effects of two training protocols on Angiotensin I-converting enzyme (ACE) activity in horses. *Equine Vet J* 43, 466-470.
38. Frisbie, D. D., Al-Sobayil, F., Billinghurst, R. C., Kawcak, C. E. and McIlwraith, C. W. (2008) Changes in synovial fluid and serum biomarkers with exercise and early osteoarthritis in horses. *Osteoarthritis Cartilage* 16, 1196-1204.
39. Graham, R. J. T. Y., Anderson, J. R., Phelan, M. M., Cillan-Garcia, E., Bladon, B. M. and Taylor, S. E. (2020) Metabolomic analysis of synovial fluid from Thoroughbred racehorses diagnosed with palmar osteochondral disease using magnetic resonance imaging. *Equine Veterinary Journal* 52, 384-390.
40. Frisbie, D. D., Mc Ilwraith, C. W., Arthur, R. M., Blea, J., Baker, V. A. and Billinghurst, R. C. (2010) Serum biomarker levels for musculoskeletal disease in two- and three-year-old racing Thoroughbred horses: A prospective study of 130 horses. *Equine Veterinary Journal* 42, 643-651.
41. Turlo, A. J., Cywinska, A. and Frisbie, D. D. (2019) Revisiting predictive biomarkers of musculoskeletal injury in thoroughbred racehorses: longitudinal study in polish population. *BMC veterinary research* 15, 66.
42. Heleski, C., Stowe, C. J., Fiedler, J., Peterson, M. L., Brady, C., Wickens, C. and MacLeod, J. N. (2020) Thoroughbred Racehorse Welfare through the Lens of 'Social License to Operate—With an Emphasis on a U.S. Perspective. *Sustainability* 12.
43. Smith, L. L. (2004) Tissue trauma: the underlying cause of overtraining syndrome? *J Strength Cond Res* 18, 185-193.
44. Nieman, D. C. and Pedersen, B. K. (1999) Exercise and Immune Function. *Sports Medicine* 27, 7380.
45. Walsh, N. P., Gleeson, M., Shephard, R. J., Gleeson, M., Woods, J. A., Bishop, N.C., Fleshner, M., Green, C., Pedersen, B. K., Hoffman-Goetz, L., Rogers, C. J., Northoff, H., Abbasi, A. and Simon, P. (2011) Position statement part one: Immune function and exercise. *Exercise immunology review* 17, 6-63.
46. Huldani, Pattelongi, I., Massi, M. N., Idris, I., Bukhari, A., Wahyu Widodo, A. D. and Achmad, H. (2020) Research Reviews on Effect of Exercise on DAMP's, HMGB1, Proinflammatory Cytokines and Leukocytes. *Systematic Reviews in Pharmacy* 11, 306-312.
47. Vezzoli, M., Castellani, P., Coma, G., Castiglioni, A., Bosurgi, L., Monno, A., Brunelli, S., Manfredi, A. A., Rubartelli, A. and Rovere-Querini, P. (2011) High-Mobility Group Box 1 Release and Redox Regulation Accompany Regeneration and Remodeling of Skeletal Muscle. *Antioxidants & Redox Signaling* 15, 2161-2174.
48. Manfredi, A. A., Capobianco, A., Bianchi, M. E. and Rovere-Querini, P. (2009) Regulation of Dendritic- and T-Cell Fate by Injury-Associated Endogenous Signals. 29, 69-86.
49. Ostrowski, K., Rohde, T., Asp, S., Schjerling, P. and Pedersen, B. K. (1999) Pro- and anti-inflammatory cytokine balance in strenuous exercise in humans. *The Journal of Physiology* 515, 287-291.
50. Philippou, A., Bogdanis, G., Maridaki, M., Halapas, A., Sourla, A. and Koutsilieris, M. (2009) Systemic cytokine response following exercise-induced muscle damage in humans. *Clinical chemistry and laboratory medicine* 47, 777-782.
51. Liburt, N. R., Adams, A. A., Betancourt, A., Horohov, D. W. and McKeever, K. H. (2010) Exercise-induced increases in inflammatory cytokines in muscle and blood of horses. *Equine Vet J Suppl* 42, 280-288.
52. Lehnhard, R., Adams, A., Betancourt, A., Horohov, D., Liburt, N., Streltsova, J., Franke, W. and McKeever, K. (2010) Phenylbutazone blocks the cytokine response following a high-intensity incremental exercise challenge in horses. *Comparative Exercise Physiology* 7, 103-108.
53. Horohov, D. W., Sinatra, S. T., Chopra, R. K., Jankowitz, S., Betancourt, A. and Bloomer, R. J. (2012) The Effect of Exercise and Nutritional Supplementation on Proinflammatory Cytokine Expression in Young Racehorses During Training. *Journal of Equine Veterinary Science* 32, 805-815.
54. Donovan, D. C., Jackson, C. A., Colahan, P. T., Norton, N. and Hurley, D. J. (2007) Exercise-induced alterations in pro-inflammatory cytokines and prostaglandin F2alpha in horses. *Vet Immunol Immunopathol* 118, 263-269.
55. Page, A. E., Stewart, J. C., Holland, R. E. and Horohov, D. W. (2017) The Impact of Training Regimen on the Inflammatory Response to Exercise in 2-Year-Old Thoroughbreds. *Journal of Equine Veterinary Science* 58, 78-83.
56. Page, A. E., Stewart, J. C., Scollay, M. C. and Horohov, D. W. (2019) Comparison of pre-race inflammatory marker mRNA expression with race-related parameters in Thoroughbreds. *Comparative Exercise Physiology* 16, 101-106.
57. Page, A. E., Adam, E., Stewart, J. C., Gonzales, C., Barker, V. and Horohov, D. W. (2020) Alterations of peripheral gene expression in response to lipopolysaccharide-induced synovitis as a model for inflammation in horses. *Veterinary Immunology and Immunopathology* 225, 110058.
58. Page, A. E., Stewart, J. C., Fielding, C. L. and Horohov, D. W. (2019) The effect of a 160-kilometer competitive endurance ride on inflammatory marker mRNA expression in horses. *Journal of Equine Veterinary Science* 79, 45-49.
59. Livak, K. J. and Schmittgen, T. D. (2001) Analysis of Relative Gene Expression Data Using Real-Time Quantitative PCR and the 2-ΔΔCT Method. *Methods (San Diego, Calif.)* 25, 402-408.
60. Breathnach, C. C., Sturgill-Wright, T., Stiltner, J. L., Adams, A. A., Lunn, D. P. and Horohov, D. W. (2006) Foals are interferon gamma-deficient at birth. *Vet Immunol Immunopathol* 112, 199-209.
61. Vick, M. M., Murphy, B. A., Sessions, D. R., Reedy, S. E., Kennedy, E. L., Horohov, D. W., Cook, R. F. and Fitzgerald, B. P. (2008) Effects of systemic inflammation on insulin sensitivity in horses and inflammatory cytokine expression in adipose tissue. *American Journal of Veterinary Research* 69, 130-139.
62. Johnson, B. J., Stover, S. M., Daft, B. M., Kinde, H., Read, D. H., Barr, B. C., Anderson, M., Moore, J., Woods, L., Stoltz, J. and Blanchard, P. (1994) Causes of death in racehorses over a 2 year period. *Equine Veterinary Journal* 26, 327-330.
63. Anthenill, L. A., Stover, S. M., Gardner, I. A., Hill, A. E., Lee, C. M., Anderson, M. L., Barr, B. C., Read, D. H., Johnson, B. J., Woods, L. W., Daft, B. M., Kinde, H., Moore, J. D., Farman, C. A., Odani, J. S., Pesavento, P. A., Uzal, F. A., Case, J. T. and Ardans, A. A. (2006) Association between findings on palmarodorsal radiographic images and detection of a fracture in the proximal sesamoid bones of forelimbs obtained from cadavers of racing Thoroughbreds. *American Journal of Veterinary Research* 67, 858-868.
64. Hernandez, J., Hawkins, D. L. and Scollay, M. C. (2001) Race-start characteristics and risk of catastrophic musculoskeletal injury in Thoroughbred racehorses. *J Am Vet Med Assoc* 218, 8386.
65. Estberg, L., Stover, S. M., Gardner, I. A., Johnson, B. J., Jack, R. A., Case, J. T., Ardans, A., Read, D. H., Anderson, M. L., Barr, B. C., Daft, B. M., Kinde, H., Moore, J., Stoltz, J. and Woods, L. (1998) Relationship between race start characteristics and risk of catastrophic injury in thoroughbreds: 78 cases (1992). *Journal of the American Veterinary Medical Association* 212, 544-549.
66. Cohen, N. D., Mundy, G. D., Peloso, J. G., Carey, V. J. and Amend, N. K. (1999) Results of physical inspection before races and race-related characteristics and their association with musculoskeletal injuries in Thoroughbreds during races. *Journal of the American Veterinary Medical Association* 215, 654-661.
67. Cohen, N. D., Dresser, B. T., Peloso, J. G., Mundy, G. D. and Woods, A. M. (1999) Frequency of musculoskeletal injuries and risk factors associated with injuries incurred in Quarter Horses during races. *J Am Vet Med Assoc* 215, 662-669.
68. Heemskerk, V. H., Daemen, M. A. R. C. and Buurman, W. A. (1999) Insulin-like growth factor-1 (IGF-1) and growth hormone (GH) in immunity and inflammation. *Cytokine & Growth Factor Reviews* 10, 5-14.
69. Majidinia, M., Sadeghpour, A. and Yousefi, B. (2018) The roles of signaling pathways in bone repair and regeneration. *Journal of Cellular Physiology* 233, 2937-2948.
70. Blumenfeld, I., Srouji, S., Peled, M. and Livne, E. (2002) Metalloproteinases (MMPs-2, -3) are involved in TGF-β and IGF-1-induced bone defect healing in 20-month-old female rats. *Archives of Gerontology and Geriatrics* 35, 59-69.
71. Lieu, S., Hansen, E., Dedini, R., Behonick, D., Werb, Z., Miclau, T., Marcucio, R. and Colnot, C. (2011) Impaired remodeling phase of fracture repair in the absence of matrix metalloproteinase-2. *Disease Models & Mechanisms* 4, 203.
72. Nieman, D. C., Henson, D. A., Davis, J. M., Dumke, C. L., Utter, A. C., Murphy, E. A., Pearce, S., Gojanovich, G., McAnulty, S. R. and McAnulty, L. S. (2006) Blood leukocyte mRNA expression for IL-10, IL-1Ra, and IL-8, but not IL-6, increases after exercise. *J Interferon Cytokine Res* 26, 668674.
73. Anthenill, L. A., Gardner, I. A., Pool, R. R., Garcia, T. C. and Stover, S. M. (2010) Comparison of macrostructural and microstructural bone features in Thoroughbred racehorses with and without midbody fracture of the proximal sesamoid bone. *Am J Vet Res* 71, 755-765.
74. Peloso, J. G., Mundy, G. D. and Cohen, N. D. (1994) Prevalence of, and factors associated with, musculoskeletal racing injuries of thoroughbreds. *J Am Vet Med Assoc* 204, 620-626.
75. Parkin, T. D. (2007) Epidemiology of training and racing injuries. *Equine Vet J* 39, 466-469.
76. Parkin, T. D. (2008) Epidemiology of racetrack injuries in racehorses. *The Veterinary clinics of North America. Equine practice* 24, 1-19.
77. Georgopoulos, S. P. and Parkin, T. D. (2016) Risk factors associated with fatal injuries in Thoroughbred racehorses competing in flat racing in the United States and Canada. *J Am Vet Med Assoc* 249, 931-939.
78. Swift, J. and G. M. Coruzzi, *A matter of time—How transient transcription factor interactions create dynamic gene regulatory networks*. Biochimica et biophysica acta. Gene regulatory mechanisms, 2017. 1860(1): p. 75-83.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of detecting biomarker expression indicative of increased risk for catastrophic injury in a non-human athletic animal, comprising:

(a) obtaining a blood sample from a subject horse;

(b) detecting in the blood sample from the subject horse the mRNA expression level of at least one of interleukin 1 receptor antagonist (IL1RN), insulin-like growth factor (IGF-1), and matrix metallopeptidase 2 (MMP2); and (c) detecting at least one of (i) a decreased mRNA expression level of IL1RN in the blood sample obtained from the subject horse relative to a control expression level of IL1RN from one or more control blood samples obtained from one or more control horses without catastrophic injury, (ii) an increased mRNA expression level of IGF-1 in the blood sample obtained from the subject horse relative to a control expression level of IGF-1 from the one or more control blood samples obtained from the one or more control horses without catastrophic injury, and (iii) an increased mRNA expression level of MMP2 in the blood sample obtained from the subject horse relative to a control expression level of MMP2 from the one or more control blood samples obtained from the one or more control horses without catastrophic injury;

(d) identifying the subject horse as being at risk for catastrophic injury based on the detection of the at least one of the decreased mRNA expression level of IL1RN in the blood sample obtained from the subject horse, the increased mRNA expression level of IGF-1 in the blood sample obtained from the subject horse, and the increased mRNA expression level of MMP2 in the blood sample obtained from the subject horse; and (e) treating the subject horse subsequent to being identified as at risk for catastrophic injury;

wherein treating the subject horse includes implementing advanced diagnostics to localize potential injury locations.

2. A method for detecting biomarker expression indicative of increased risk for catastrophic injury in a non-human athletic animal, comprising:

(a) obtaining a first blood sample from a subject horse;

(b) detecting in the first blood sample from the subject horse the mRNA expression level of at least one of interleukin 1 receptor antagonist (IL1RN), insulin-like growth factor (IGF-1), and matrix metallopeptidase 2 (MMP2);

(c) obtaining a second blood sample from the subject horse at a time subsequent to when the first blood sample was obtained; and (d) detecting in the second blood sample the mRNA expression level of at least one of IL1RN, IGF-1, and MMP2; and (e) detecting at least one of (i) a decreased level of IL1RN in the second blood sample obtained from the subject horse relative to the expression level of IL1RN in the first blood sample, (ii) an increased level of IGF-1 in the second blood sample obtained from the subject horse relative to the expression level of IGF-1 in the first blood sample, and (iii) an increased level of MMP2 in the second blood sample obtained from the subject horse relative to the expression level of MMP2 in the first blood sample;

(f) identifying the subject horse as being at risk for catastrophic injury based on the detection of the at least one of the decreased mRNA expression level of IL1RN in the second blood sample obtained from the subject horse, the increased mRNA expression level of IGF-1 in the second blood sample obtained from the subject horse, and the increased mRNA expression level of MMP2 in the second blood sample obtained from the subject horse;

(g) treating the subject horse subsequent to being identified as at risk for catastrophic injury;

wherein treating the subject horse includes implementing advanced diagnostics to localize potential injury locations.

3. The method of claim 1, wherein the blood sample from the subject horse is from whole peripheral blood.

4. The method of claim 3, wherein the blood sample from the subject horse is plasma or serum from the whole peripheral blood.

5. The method of claim 3, wherein the blood sample from the subject horse is a buffy coat fraction of the whole peripheral blood.

6. The method of claim 1, and further comprising extracting mRNA from the blood sample from the subject horse.

7. The method of claim 6, and further comprising measuring in the extracted mRNA the levels of mRNA corresponding to the at least one of IL1RN, IGF-1, and MMP2.

8. The method of claim 7, wherein quantitative polymerase chain reaction (qPCR) is used to measure the mRNA by measuring cDNA of the mRNA.

9. The method of claim 1, wherein an increased expression level of at least one of IGF-1 and MMP2 in the blood sample from the subject animal is detected relative to the control expression level of a corresponding gene of the one or more control blood samples obtained from the one or more control animals without catastrophic injury.

10. The method of claim 2, wherein an increased mRNA expression level of at least one of IGF-1 and MMP2 in the first blood sample is detected relative to the mRNA expression level of an mRNA expression level of a corresponding gene in the second blood sample.

* * * * *

SEQUENCE LISTING

<160> NUMBER OF SEQ ID NOS: 14

<210> SEQ ID NO 1
<211> LENGTH: 612
<212> TYPE: DNA
<213> ORGANISM: Artificial Sequence
<220> FEATURE:
<223> OTHER INFORMATION: Recombinant

<400> SEQUENCE: 1

```
caggcctggg gtggcacgga gctggagcag tcctcactgc ggggagcctg gagcgaacat      60
ggatcaagaa accgtgggca atgttgtcct gctggccatc gtcaccctca ttagcgtgat     120
ccagaatggg ttcttcgccc acaaggtgga acacgaaagc aagactcaga atgggcggag     180
cttccagagg acgggaacac ttgcctttga gcgggtctac actgccaacc aaaactgtgt     240
agacgcgtat cccactttcc ttgtcatgct ctggagcgcc gggctactct gcagccaagt     300
tcctgccgcc tttgctgggc tgatgtacct gttcgtgagg cagaagtact tcgtgggcta     360
tctgggagag agaaggcaga gcacacccgg ctacatattt gggaaacgca tcatactgtt     420
cctgttcctc atgtcccttg ctggaatatt caactattat ctcatcctct ttttcggaag     480
tgactttgaa aactacataa agacgataac caccaccatc tcccctctac ttctcattcc     540
ctaactctct gctgaataca gggttggtgc tctcatctaa tcaataccta aatcatcata     600
actcaactcc ta                                                         612
```

<210> SEQ ID NO 2
<211> LENGTH: 161
<212> TYPE: PRT
<213> ORGANISM: Artificial Sequence
<220> FEATURE:
<223> OTHER INFORMATION: Recombinant

<400> SEQUENCE: 2

```
Met Asp Gln Glu Thr Val Gly Asn Val Val Leu Leu Ala Ile Val Thr
1               5                   10                  15

Leu Ile Ser Val Ile Gln Asn Gly Phe Phe Ala His Lys Val Glu His
            20                  25                  30

Glu Ser Lys Thr Gln Asn Gly Arg Ser Phe Gln Arg Thr Gly Thr Leu
        35                  40                  45

Ala Phe Glu Arg Val Tyr Thr Ala Asn Gln Asn Cys Val Asp Ala Tyr
    50                  55                  60

Pro Thr Phe Leu Val Met Leu Trp Ser Ala Gly Leu Leu Cys Ser Gln
65                  70                  75                  80

Val Pro Ala Ala Phe Ala Gly Leu Met Tyr Leu Phe Val Arg Gln Lys
                85                  90                  95

Tyr Phe Val Gly Tyr Leu Gly Glu Arg Arg Gln Ser Thr Pro Gly Tyr
            100                 105                 110

Ile Phe Gly Lys Arg Ile Ile Leu Phe Leu Phe Leu Met Ser Leu Ala
        115                 120                 125

Gly Ile Phe Asn Tyr Tyr Leu Ile Leu Phe Phe Gly Ser Asp Phe Glu
    130                 135                 140

Asn Tyr Ile Lys Thr Ile Thr Thr Thr Ile Ser Pro Leu Leu Leu Ile
145                 150                 155                 160

Pro
```

<210> SEQ ID NO 3
<211> LENGTH: 510

```
<212> TYPE: DNA
<213> ORGANISM: Artificial Sequence
<220> FEATURE:
<223> OTHER INFORMATION: Recombinant

<400> SEQUENCE: 3
tgcacttcag aagcaatggg aaaaatcagc agtcttccaa cccaattatt taagtgctgc      60
ttttgtgatt tcttgaaggt aaagatgcac atcatgtcct cctcacatct cttctacctg     120
gccctgtgct tgctcacctt caccagctct gccacggctg accggagac actctgcggg      180 gctgagctgg tggacgctct tcagttcgtg tgtggagaca ggggctttta tttcaacaag     240
cccacagggt acggctccag cagtcggagg gcgcctcaga caggcatcgt ggacgagtgc     300
tgcttccgga gctgtgatct gaggaggctg gagatgtact gcgcacccct caagcctgcc     360
aagtcggccc gctccgtccg tgcccagcgc acaccgata tgcccaaggc tcagaaggaa      420
gtacatttga agaacgcaag tagagggagt gcgggaaaca agaactacag aatgtaggaa     480
gactcccctc gagtgaagaa tgccatgcca                                       510

<210> SEQ ID NO 4
<211> LENGTH: 153
<212> TYPE: PRT
<213> ORGANISM: Artificial Sequence
<220> FEATURE:
<223> OTHER INFORMATION: Recombinant

<400> SEQUENCE: 4

Met Gly Lys Ile Ser Ser Leu Pro Thr Gln Leu Phe Lys Cys Cys Phe
1               5                   10                  15

Cys Asp Phe Leu Lys Val Lys Met His Ile Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Ala Gln Lys Glu Val His Leu Lys Asn Ala Ser Arg Gly
    130                 135                 140

Ser Ala Gly Asn Lys Asn Tyr Arg Met
145                 150

<210> SEQ ID NO 5
<211> LENGTH: 745
<212> TYPE: DNA
<213> ORGANISM: Artificial Sequence
<220> FEATURE:
<223> OTHER INFORMATION: Recombinant

<400> SEQUENCE: 5
atgaactcct tcttcacaag caccgtcact ccagttgcct tctccctggg gctgctcctg      60
gtgatggcta ctgctttccc caccccacta cccctgggag aagatgaaac cacctcaaat     120
```

```
ggaccactac tcaccactgc agacaaaacc aaacagcaca ttaagtacat cctcggcaaa    180
atctctgccc tgaaaaatga gatgtgtaac aattttagca agtgtgaaaa cagcaaggag    240
gtactggcag aaaacaacct gaatcttcca agatggcag aaaaagacgg atgcttccaa     300
tctgggttca atcaggagac ctgcctgatg aaaatcacca ctggtctttc ggagtttcag    360
atatacctgg agtacctcca gaacgagttc aagggtgaaa aggaaaacat caagactatg    420
cagatcagta ccaaagtcct ggtccagatc ctgatgcaaa agatgaagaa tccagaagta    480 accaccctg acccaactgc aaaaagcagc ctgctggcta agctgcattc acagaatgag     540
tggctgaaga cacaacaac tcacctcatc cttcgaagcc ttgaggattt cctgcagttc     600
agcctgagag ctgttcggat aatgtaacct tggcatctaa gattgttgta gttcatgggc    660
attccttcct ctggtcagaa acctgtccac tgggcacata acttatgttg ttctctatga    720
agaactaaaa gtatgagcgt tagga                                          745
```

<210> SEQ ID NO 6
<211> LENGTH: 208
<212> TYPE: PRT
<213> ORGANISM: Artificial Sequence
<220> FEATURE:
<223> OTHER INFORMATION: Recombinant

<400> SEQUENCE: 6

```
Met Asn Ser Phe Phe Thr Ser Thr Val Thr Pro Val Ala Phe Ser Leu
1               5                   10                  15

Gly Leu Leu Leu Val Met Ala Thr Ala Phe Pro Thr Pro Leu Pro Leu
            20                  25                  30

Gly Glu Asp Glu Thr Thr Ser Asn Gly Pro Leu Leu Thr Thr Ala Asp
        35                  40                  45

Lys Thr Lys Gln His Ile Lys Tyr Ile Leu Gly Lys Ile Ser Ala Leu
    50                  55                  60

Lys Asn Glu Met Cys Asn Asn Phe Ser Lys Cys Glu Asn Ser Lys Glu
65                  70                  75                  80

Val Leu Ala Glu Asn Asn Leu Asn Leu Pro Lys Met Ala Glu Lys Asp
                85                  90                  95

Gly Cys Phe Gln Ser Gly Phe Asn Gln Glu Thr Cys Leu Met Lys Ile
            100                 105                 110

Thr Thr Gly Leu Ser Glu Phe Gln Ile Tyr Leu Glu Tyr Leu Gln Asn
        115                 120                 125

Glu Phe Lys Gly Glu Lys Glu Asn Ile Lys Thr Met Gln Ile Ser Thr
    130                 135                 140

Lys Val Leu Val Gln Ile Leu Met Gln Lys Met Lys Asn Pro Glu Val
145                 150                 155                 160

Thr Thr Pro Asp Pro Thr Ala Lys Ser Ser Leu Leu Ala Lys Leu His
                165                 170                 175

Ser Gln Asn Glu Trp Leu Lys Asn Thr Thr His Leu Ile Leu Arg
            180                 185                 190

Ser Leu Glu Asp Phe Leu Gln Phe Ser Leu Arg Ala Val Arg Ile Met
        195                 200                 205
```

<210> SEQ ID NO 7
<211> LENGTH: 1156
<212> TYPE: DNA
<213> ORGANISM: Artificial Sequence
<220> FEATURE:
<223> OTHER INFORMATION: Recombinant

<400> SEQUENCE: 7

```
aactataact tcttcccccg caagcccaag tgggagaaaa cccagatcac atacaggatc    60
atcggctaca cacctgatct ggaccctgag acggtggatg atgccttcgc tcgtgccttc   120
cgagtctgga gtgatgtgac cccactacgg ttttctcgca tccatgatgg agaggctgac   180
atcatgatca acttcggccg ctgggagcac ggagatgggt accccttga tggcaaggat    240
gggctcctgg ctcacgcctt tgccccgggc cctggtgttg ggggagactc ccactttgat   300
gacgacgagc tgtggaccct gggagaaggg caagtggtcc gtgtgaagta tggcaacgcc   360
gacggggagt actgcaagtt ccccttcctc ttcaacggca aggagtacac cagctgcacc   420
gacacgggcc gcagcgacgg cttcctctgg tgctccacca cctacaactt cgacaaggac   480
ggcaaatacg gcttctgccc ccatgaagcc ctgttcacca tgggtggcaa cgccgacgga   540
cagccctgca agttcccgtt ccgcttccag ggcacatcct acgacagctg caccaccgag   600
ggccgcaccg acggctaccg ctggtgtggc accaccgagg actacgaccg tgacaagaag   660
tacggcttct gccccgagac cgccatgtcc accgttggcg ggaactcgga aggtgcccccc  720
tgtgtcttcc ccttcacctt cctgggcaac aagcatgagg gctgcaccag cgccggccgc   780
agtgacggga agatgtggtg cgcgactaca gccaactacg atgacgaccg aaagtggggc   840
ttctgccctg accagggta cagcctgttc ttggtggcag cccatgagtt tggccatgcc    900
atggggctgg agcactcaca ggaccctgga ccctgatgg cgcccattta cacgtacacc    960
aagcacttcc gcctgtccca tgatgacatc aagggcattc aagagctcta cgggggctcc  1020
cctgacactg gcacggacgc tggcaccggc cccaccccca cgctgggacc tgtcactcct  1080
gagatctgca agcaggacat tgtctttgac ggcatctctc agatccgggg ggagatcttc  1140
ttcttcaagg accggt                                                   1156
```

<210> SEQ ID NO 8
<211> LENGTH: 385
<212> TYPE: PRT
<213> ORGANISM: Artificial Sequence
<220> FEATURE:
<223> OTHER INFORMATION: Recombinant

<400> SEQUENCE: 8

```
Asn Tyr Asn Phe Phe Pro Arg Lys Pro Lys Trp Glu Lys Thr Gln Ile
1               5                   10                  15

Thr Tyr Arg Ile Ile Gly Tyr Thr Pro Asp Leu Asp Pro Glu Thr Val
            20                  25                  30

Asp Asp Ala Phe Ala Arg Ala Phe Arg Val Trp Ser Asp Val Thr Pro
        35                  40                  45

Leu Arg Phe Ser Arg Ile His Asp Gly Glu Ala Asp Ile Met Ile Asn
    50                  55                  60

Phe Gly Arg Trp Glu His Gly Asp Gly Tyr Pro Phe Asp Gly Lys Asp
65                  70                  75                  80

Gly Leu Leu Ala His Ala Phe Ala Pro Gly Pro Gly Val Gly Gly Asp
                85                  90                  95

Ser His Phe Asp Asp Asp Glu Leu Trp Thr Leu Gly Glu Gly Gln Val
            100                 105                 110

Val Arg Val Lys Tyr Gly Asn Ala Asp Gly Glu Tyr Cys Lys Phe Pro
        115                 120                 125

Phe Leu Phe Asn Gly Lys Glu Tyr Thr Ser Cys Thr Asp Thr Gly Arg
    130                 135                 140
```

```
Ser Asp Gly Phe Leu Trp Cys Ser Thr Thr Tyr Asn Phe Asp Lys Asp
145                 150                 155                 160

Gly Lys Tyr Gly Phe Cys Pro His Glu Ala Leu Phe Thr Met Gly Gly
                165                 170                 175

Asn Ala Asp Gly Gln Pro Cys Lys Phe Pro Phe Arg Phe Gln Gly Thr
            180                 185                 190

Ser Tyr Asp Ser Cys Thr Thr Glu Gly Arg Thr Asp Gly Tyr Arg Trp
        195                 200                 205

Cys Gly Thr Thr Glu Asp Tyr Asp Arg Asp Lys Lys Tyr Gly Phe Cys
210                 215                 220

Pro Glu Thr Ala Met Ser Thr Val Gly Gly Asn Ser Glu Gly Ala Pro
225                 230                 235                 240

Cys Val Phe Pro Phe Thr Phe Leu Gly Asn Lys His Glu Gly Cys Thr
                245                 250                 255

Ser Ala Gly Arg Ser Asp Gly Lys Met Trp Cys Ala Thr Thr Ala Asn
            260                 265                 270

Tyr Asp Asp Asp Arg Lys Trp Gly Phe Cys Pro Asp Gln Gly Tyr Ser
        275                 280                 285

Leu Phe Leu Val Ala Ala His Glu Phe Gly His Ala Met Gly Leu Glu
    290                 295                 300

His Ser Gln Asp Pro Gly Ala Leu Met Ala Pro Ile Tyr Thr Tyr Thr
305                 310                 315                 320

Lys His Phe Arg Leu Ser His Asp Asp Ile Lys Gly Ile Gln Glu Leu
                325                 330                 335

Tyr Gly Gly Ser Pro Asp Thr Gly Thr Asp Ala Gly Thr Gly Pro Thr
            340                 345                 350

Pro Thr Leu Gly Pro Val Thr Pro Glu Ile Cys Lys Gln Asp Ile Val
        355                 360                 365

Phe Asp Gly Ile Ser Gln Ile Arg Gly Glu Ile Phe Phe Phe Lys Asp
    370                 375                 380

Arg
385

<210> SEQ ID NO 9
<211> LENGTH: 1646
<212> TYPE: DNA
<213> ORGANISM: Artificial Sequence
<220> FEATURE:
<223> OTHER INFORMATION: Recombinant

<400> SEQUENCE: 9
ataagcagct cctccgagcc cgaaatggca ctctcccgtt gccttgttgt ggccacagga      60
tggaaatccg caggcgttct gtcagacacc taatctctct cctccttttc ttgctctact     120
cagagacagc ctgccaccct tggggaaga gaccctgcaa gatgcaagcc ttcagaatct      180
gggatgttaa ccagaagacc ttctacatga ggaataacca actagttgct ggatacttgc     240
aagaatcaaa tactaaatta caagagaaga tagatgtggt gcccattgag cctgatgctc     300
tattcctggg actccatggg aggaagctgt gcctggcctg tgtcaagtct ggtgatgaga     360
ttaggttcca attggaggca gttaacatca ctgacctgag caagaacaag gaggagaaca     420
agcgcttcac cttcatccgc tcaaacagtg gccccaccac cagcttcgag tctgccgcct     480
gccctggctg gttcctctgc acggcgcagg aggcagaccg gccgtcagc ctcaccaaca     540 agcccaaaga gtccttcatg gtcaccaagt tctacctcca ggaggaccag tagaactgcc     600
cgtagctccg cttcccctat tcccagcacg tcgatgactc cagagactgc ctctccaccc     660
```

-continued

```
cagggtctcc tggggctctg aggagcagcc ttggcagggt gggccctcag aaggaggtac    720
acgagccctc gtaacaggac tctgtctcca gcctcctcag ctatcccacc ctccatgctg    780
cttccaccat ggtctttcta aagtgcagct caaaccacgg ccctacttaa agcccttcag    840
tgtcgtctgt accttcagga taaaatccgg gccacctggc cagcctggat gccctctgct    900
ctcctctctc aagtcttcct tctccctcac cccactgtcc ctgcccgaga tccctcaggc    960
cactcactgg cccccaccaa atggctctca taccttgttt tggaatctga tgctgttctg   1020
tagggaagac ttttagagtc tgtggcaaaa tggaaaataa gaatttcatg aaactttcta   1080
aagccagctt tatccaattt gaaggagagt cctttatttg gagattattt ccttttttgca  1140 aaggggtggg gatcaaaata ttcctgtgtt tgtgaagtga tagtgaaggg aggttccctt   1200
gttagtgtcc attcttgttt ttgtaatacc ctaaccggta aaaatgaaca gttagtgtac   1260
tatgtttgtc ccttattctt ttctttctga acgttcctg taagtctgga cccactgccc    1320
gggcctgagc accacctcca ttgcagacct tcacagctg cccacagtgc tttcccctcc    1380
catcaaaggt tcccctgctc ccacggcaca gcacaaatgt ggctcctcca aggcctttcc   1440
tgatctcccg ggaggaatga atcgctcctt gaccatttta gcacttctga cgctctgaaa   1500
cttgtttgaa aggtggttat gcctctgtct gtctcctgcc ccaaactgtg agctcctgga   1560
agcagggaac atgactggca tgtgtctcag cttcccccag ggccaagcac atggcctgtt   1620
ttacaataaa accttgaaat tcatct                                        1646
```

<210> SEQ ID NO 10
<211> LENGTH: 177
<212> TYPE: PRT
<213> ORGANISM: Artificial Sequence
<220> FEATURE:
<223> OTHER INFORMATION: Recombinant

<400> SEQUENCE: 10

```
Met Glu Ile Arg Arg Ser Val Arg His Leu Ile Ser Leu Leu Leu
1               5                   10                  15

Phe Leu Leu Tyr Ser Glu Thr Ala Cys His Pro Leu Gly Lys Arg Pro
                20                  25                  30

Cys Lys Met Gln Ala Phe Arg Ile Trp Asp Val Asn Gln Lys Thr Phe
            35                  40                  45

Tyr Met Arg Asn Asn Gln Leu Val Ala Gly Tyr Leu Gln Glu Ser Asn
        50                  55                  60

Thr Lys Leu Gln Glu Lys Ile Asp Val Val Pro Ile Glu Pro Asp Ala
65                  70                  75                  80

Leu Phe Leu Gly Leu His Gly Arg Lys Leu Cys Leu Ala Cys Val Lys
                85                  90                  95

Ser Gly Asp Glu Ile Arg Phe Gln Leu Glu Ala Val Asn Ile Thr Asp
                100                 105                 110

Leu Ser Lys Asn Lys Glu Glu Asn Lys Arg Phe Thr Phe Ile Arg Ser
            115                 120                 125

Asn Ser Gly Pro Thr Thr Ser Phe Glu Ser Ala Ala Cys Pro Gly Trp
        130                 135                 140

Phe Leu Cys Thr Ala Gln Glu Ala Asp Arg Pro Val Ser Leu Thr Asn
145                 150                 155                 160

Lys Pro Lys Glu Ser Phe Met Val Thr Lys Phe Tyr Leu Gln Glu Asp
                165                 170                 175

Gln
```

<210> SEQ ID NO 11
<211> LENGTH: 2151
<212> TYPE: DNA
<213> ORGANISM: Artificial Sequence
<220> FEATURE:
<223> OTHER INFORMATION: Recombinant

<400> SEQUENCE: 11

| | | | | | | |
|---|---|---|---|---|---|---|
| atgagcccct | ggcagccctt | ggtcctggcg | gtcttggcgc | tgggctgctg | ctctgccgcc | 60 |
| cctacacggc | accagcccac | cgtggtggtc | ttcccaggag | acctgctaac | taacctcact | 120 |
| gacagggagc | tggcagagga | atatctgttc | cgctatggct | acactggtgt | cgccgagatg | 180 |
| agcgagggcg | atcagcccct | ggagcgggcg | ctgcggagac | tccagaagcg | cctggccctg | 240 |
| cccgagactg | gcgagctgga | cagcaccacc | ctggaggcca | tgcgtacccc | gcgctgcggc | 300 |
| gtcccaggcg | tgggccagtt | ccagaccttt | gagggcgacc | tcaagtggca | ccaccgcgac | 360 |
| atcacgtact | ggatccaaaa | ctactcggga | gacttgccgc | gcgacgtgat | cgacgacgcc | 420 |
| tttgcccgcg | ccttcgcggt | ctggagcgag | gtgacgccgc | tcaccttcac | ccgcgtgaac | 480 |
| ggcccgcaag | ccgatatcgt | catccagttt | ggcgttaggg | agcacggaga | tgggtatccc | 540 |
| ttcgatggga | aggacgggct | cctggcacac | gcctttcccc | ctggtcccgg | cattcaggga | 600 |
| gacgcccact | cgacgacga | agagttgtgg | tctctgggca | agggcccgt | ggttccaacg | 660 |
| cactttggaa | acgcagatgg | cgcccctgc | cacttcccct | tcaccttcga | gggccgctcc | 720 |
| tactcctctt | gcaccacgga | cggccgctcg | gacgacatgc | tctggtgcag | caccacggcc | 780 |
| tactatgaca | ccgaccgccg | gtttggtttc | tgccccagcg | agaaactcta | cacccaggac | 840 |
| ggcaatgccg | acggcaagcc | ctgcgtgttt | cccttcacct | tcgagggtcg | ctcctactcc | 900 |
| acctgcacca | ccgacggccg | ctcggatggg | taccgctggt | gcgccactac | cgccaactac | 960 |
| gaccaggaca | agcgttatgg | cttctgcccg | acccgagttg | actccacagt | gaacggggc | 1020 |
| aactccgccg | gggagctgtg | cgtcttcccc | ttcaccttcc | tgggcaagga | gtactctgcc | 1080 |
| tgtaccagag | agggccgcag | tgatgggcgc | tctggtgcg | ccaccacctc | gaacttcgac | 1140 |
| agcgacaaga | agtgggcctt | ctgccccgac | caaggataca | gcctgttcct | cgtggcggcg | 1200 |
| catgagttcg | gccacgcact | gggcctagat | cactcatccg | tgccagcggc | gctcatgtac | 1260 |
| cccatgtaca | gcttcaccga | ggagcccccg | ctgcatgagg | acgatgtgaa | cggcatccag | 1320 |
| tatctctatg | gtcctcgccc | taaacctgaa | ccccagcctc | caaccaccac | cacactggaa | 1380 |
| cctcagacga | cagtctgtgc | tactgggcct | cccactactc | gccttcaga | gcgcccact | 1440 |
| gctggccca | caggccccc | ttcagctggc | ccacgggtc | ccccagtgc | tggccctccc | 1500 |
| acgggtcccc | ccactgctgg | ccctccaca | gccccaacag | tgcctttggg | tccagggag | 1560 |
| gaggtctgca | acgtggacat | cttcgatgcc | atcgcggaga | tcgggaatca | tctccatttc | 1620 |
| ttcaaggacg | ggaggtactg | gcgactcttg | gagggcaagg | gacgcgggt | gcagggcccc | 1680 |
| ttcctgatca | gggacacatg | gcctatgctg | cccccaagc | tggattccgc | ctttgaggag | 1740 |
| ccactcacca | gaagattttt | cttcttctct | gggcgccaag | tgtgggtgta | cacaggcaag | 1800 |
| tcggcgctag | gccgaggcg | tctggacaag | ctgggcctgg | gcgcggacgt | ggcccaaatc | 1860 |
| acggggcgc | tcccgcgcgg | cggcggtaag | gtgctgctgt | cagcaggcg | gcgcttctgg | 1920 |
| aggttcgacg | tgaagacaca | gaccgtggat | cccggagtg | tcagcccggt | ggaccagatg | 1980 |
| ttccccggcg | tgcccttgga | catgcacgac | gtcttccagt | accgagagaa | agcttacttc | 2040 |

```
tcccaggacc gcttctactg gcgcgtgagt tcccggaatg agatgaacca ggtggaccaa    2100
gtgggctacg tgagcttcga ccttctgcag tgccctgagg actaggggtc a             2151
```

<210> SEQ ID NO 12
<211> LENGTH: 714
<212> TYPE: PRT
<213> ORGANISM: Artificial Sequence
<220> FEATURE:
<223> OTHER INFORMATION: Recombinant

<400> SEQUENCE: 12

```
Met Ser Pro Trp Gln Pro Leu Val Leu Ala Val Leu Ala Leu Gly Cys
1               5                   10                  15

Cys Ser Ala Ala Pro Thr Arg His Gln Pro Thr Val Val Phe Pro
            20                  25                  30

Gly Asp Leu Leu Thr Asn Leu Thr Asp Arg Glu Leu Ala Glu Glu Tyr
        35                  40                  45

Leu Phe Arg Tyr Gly Tyr Thr Gly Val Ala Glu Met Ser Glu Gly Asp
    50                  55                  60

Gln Pro Leu Glu Arg Ala Leu Arg Arg Leu Gln Lys Arg Leu Ala Leu
65                  70                  75                  80

Pro Glu Thr Gly Glu Leu Asp Ser Thr Thr Leu Glu Ala Met Arg Thr
                85                  90                  95

Pro Arg Cys Gly Val Pro Gly Val Gly Gln Phe Gln Thr Phe Glu Gly
            100                 105                 110

Asp Leu Lys Trp His His Arg Asp Ile Thr Tyr Trp Ile Gln Asn Tyr
        115                 120                 125

Ser Gly Asp Leu Pro Arg Asp Val Ile Asp Asp Ala Phe Ala Arg Ala
    130                 135                 140

Phe Ala Val Trp Ser Glu Val Thr Pro Leu Thr Phe Thr Arg Val Asn
145                 150                 155                 160

Gly Pro Gln Ala Asp Ile Val Ile Gln Phe Gly Val Arg Glu His Gly
                165                 170                 175

Asp Gly Tyr Pro Phe Asp Gly Lys Asp Gly Leu Leu Ala His Ala Phe
            180                 185                 190

Pro Pro Gly Pro Gly Ile Gln Gly Asp Ala His Phe Asp Asp Glu Glu
        195                 200                 205

Leu Trp Ser Leu Gly Lys Gly Pro Val Val Pro Thr His Phe Gly Asn
    210                 215                 220

Ala Asp Gly Ala Pro Cys His Phe Pro Phe Thr Phe Glu Gly Arg Ser
225                 230                 235                 240

Tyr Ser Ser Cys Thr Thr Asp Gly Arg Ser Asp Asp Met Leu Trp Cys
                245                 250                 255

Ser Thr Thr Ala Tyr Tyr Asp Thr Asp Arg Arg Phe Gly Phe Cys Pro
            260                 265                 270

Ser Glu Lys Leu Tyr Thr Gln Asp Gly Asn Ala Asp Gly Lys Pro Cys
        275                 280                 285

Val Phe Pro Phe Thr Phe Glu Gly Arg Ser Tyr Ser Thr Cys Thr Thr
    290                 295                 300

Asp Gly Arg Ser Asp Gly Tyr Arg Trp Cys Ala Thr Ala Asn Tyr
305                 310                 315                 320

Asp Gln Asp Lys Arg Tyr Gly Phe Cys Pro Thr Arg Val Asp Ser Thr
                325                 330                 335

Val Asn Gly Gly Asn Ser Ala Gly Glu Leu Cys Val Phe Pro Phe Thr
            340                 345                 350
```

Phe Leu Gly Lys Glu Tyr Ser Ala Cys Thr Arg Glu Gly Arg Ser Asp
            355                 360                 365

Gly Arg Leu Trp Cys Ala Thr Thr Ser Asn Phe Asp Ser Asp Lys Lys
    370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Ala
                405                 410                 415

Ala Leu Met Tyr Pro Met Tyr Ser Phe Thr Glu Pro Pro Leu His
            420                 425                 430

Glu Asp Asp Val Asn Gly Ile Gln Tyr Leu Tyr Gly Pro Arg Pro Lys
            435                 440                 445

Pro Glu Pro Gln Pro Pro Thr Thr Thr Leu Glu Pro Gln Thr Thr
            450                 455                 460

Val Cys Ala Thr Gly Pro Pro Thr Thr Arg Pro Ser Glu Arg Pro Thr
465                 470                 475                 480

Ala Gly Pro Thr Gly Pro Pro Ser Ala Gly Pro Thr Gly Pro Pro Ser
                485                 490                 495

Ala Gly Pro Pro Thr Gly Pro Thr Ala Gly Pro Ser Thr Ala Pro
            500                 505                 510

Thr Val Pro Leu Gly Pro Gly Glu Glu Val Cys Asn Val Asp Ile Phe
            515                 520                 525

Asp Ala Ile Ala Glu Ile Gly Asn His Leu His Phe Phe Lys Asp Gly
            530                 535                 540

Arg Tyr Trp Arg Leu Glu Gly Lys Gly Arg Gly Val Gln Gly Pro
545                 550                 555                 560

Phe Leu Ile Arg Asp Thr Trp Pro Met Leu Pro Pro Lys Leu Asp Ser
                565                 570                 575

Ala Phe Glu Glu Pro Leu Thr Lys Lys Ile Phe Phe Phe Ser Gly Arg
            580                 585                 590

Gln Val Trp Val Tyr Thr Gly Lys Ser Ala Leu Gly Pro Arg Arg Leu
            595                 600                 605

Asp Lys Leu Gly Leu Gly Ala Asp Val Ala Gln Ile Thr Gly Ala Leu
            610                 615                 620

Pro Arg Gly Gly Gly Lys Val Leu Leu Phe Ser Arg Arg Phe Trp
625                 630                 635                 640

Arg Phe Asp Val Lys Thr Gln Thr Val Asp Pro Arg Ser Val Ser Pro
                645                 650                 655

Val Asp Gln Met Phe Pro Gly Val Pro Leu Asp Met His Asp Val Phe
            660                 665                 670

Gln Tyr Arg Glu Lys Ala Tyr Phe Ser Gln Asp Arg Phe Tyr Trp Arg
            675                 680                 685

Val Ser Ser Arg Asn Glu Met Asn Gln Val Asp Gln Val Gly Tyr Val
            690                 695                 700

Ser Phe Asp Leu Leu Gln Cys Pro Glu Asp
705                 710

<210> SEQ ID NO 13
<211> LENGTH: 624
<212> TYPE: DNA
<213> ORGANISM: Artificial Sequence
<220> FEATURE:
<223> OTHER INFORMATION: Recombinant

<400> SEQUENCE: 13

-continued

```
agccggagag ggagcgtgag ccgcgccggc cccggccggg cctccgaaac catgaacttt    60
ctgctctctt gggtgcattg gagccttgcc ttgctgctct acctccacca tgccaagtgg   120
tcccaggctg cacccatggc agaaggagag cataaaaccc atgaagtggt gaagttcatg   180
gacgtctacc agcgcagcta ctgccgtcca atcgagaccc tggtggacat cttccaggag   240
taccccgatg agatcgagta catcttcaag ccatcctgtg tgcccctgat gcggtgtggg   300
ggctgctgca acgacgaggg cctagagtgc gtgcccactg cggagttcaa catcaccatg   360
cagattatgc ggatcaaacc tcaccaaagc caacacatag gagagatgag tttcctacag   420
catagcaaat gtgaatgcag accaaagaaa gataaagcaa ggcaagaaaa tccctgtggg   480
ccttgctcag agcggagaaa gcatttgttt gtacaagatc cgcagacgtg taaatgttcc   540
tgcaaaaaca cagactcgcg ttgcaaggcg aggcagcttg agttaaacga acgtacttgc   600
agatgtgaca agccgaggcg gtga                                           624
```

<210> SEQ ID NO 14
<211> LENGTH: 190
<212> TYPE: PRT
<213> ORGANISM: Artificial Sequence
<220> FEATURE:
<223> OTHER INFORMATION: Recombinant

<400> SEQUENCE: 14

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Glu His Lys Thr His Glu Val Val Lys Phe Met Asp Val Tyr Gln Arg
        35                  40                  45

Ser Tyr Cys Arg Pro Ile Glu Thr Leu Val Asp Ile Phe Gln Glu Tyr
    50                  55                  60

Pro Asp Glu Ile Glu Tyr Ile Phe Lys Pro Ser Cys Val Pro Leu Met
65                  70                  75                  80

Arg Cys Gly Gly Cys Cys Asn Asp Glu Gly Leu Glu Cys Val Pro Thr
                85                  90                  95

Ala Glu Phe Asn Ile Thr Met Gln Ile Met Arg Ile Lys Pro His Gln
            100                 105                 110

Ser Gln His Ile Gly Glu Met Ser Phe Leu Gln His Ser Lys Cys Glu
        115                 120                 125

Cys Arg Pro Lys Lys Asp Lys Ala Arg Gln Glu Asn Pro Cys Gly Pro
    130                 135                 140

Cys Ser Glu Arg Arg Lys His Leu Phe Val Gln Asp Pro Gln Thr Cys
145                 150                 155                 160

Lys Cys Ser Cys Lys Asn Thr Asp Ser Arg Cys Lys Ala Arg Gln Leu
                165                 170                 175

Glu Leu Asn Glu Arg Thr Cys Arg Cys Asp Lys Pro Arg Arg
            180                 185                 190
```